US007771943B2

(12) United States Patent
Blanksby et al.

(10) Patent No.: US 7,771,943 B2
(45) Date of Patent: Aug. 10, 2010

(54) METHOD FOR THE DETERMINATION OF THE POSITION OF UNSATURATION IN A COMPOUND

(75) Inventors: Stephen James Blanksby, Corrimal East (AU); David Grant Harman, Keiraville (AU); Michael Christopher Thomas, Minnamurra (AU); Todd William Mitchell, Albion Park (AU)

(73) Assignee: The University of Wollongong, New South Wales (AU)

( * ) Notice: Subject to any disclaimer, the term of this patent is extended or adjusted under 35 U.S.C. 154(b) by 431 days.

(21) Appl. No.: 11/843,199

(22) Filed: Aug. 22, 2007

(65) Prior Publication Data

US 2008/0296486 A1 Dec. 4, 2008

(30) Foreign Application Priority Data

Jun. 4, 2007 (AU) .............................. 2007902993

(51) Int. Cl.
*C12Q 1/68* (2006.01)

(52) U.S. Cl. ................................ 435/6; 435/7.1; 435/4; 435/91.1

(58) Field of Classification Search ................. 250/282; 435/7.1, 4, 6, 86, 87, 173; 436/517
See application file for complete search history.

(56) References Cited

OTHER PUBLICATIONS

Mitchell, "Flying fat! Lipid mass spectrometry", University of Wollongong, CRV, Presentation (Feb. 14, 2007).

Thomas et al, "Ozone induced Dissociation (OzID): A novel method for on-line identification of double bond position within unsaturated lipids", Presentation, Univ of Wollongong, Australia (Jun. 4, 2007).

Thomas et al, "Ozone Induced Dissociation (OzID): A novel method for on-line identification of double bond position within unsaturated lipids", Presentation, Univ of Wollongong, Australia (Jul. 31. 2007).

Thomas et al, "Ozone Induced Dissociation (OzID): On-line identification of double bond position within unsaturated lipids", Presentation, Univ of Wollongong, Australia; York University, Canada (Aug. 7, 2007).

Michael C.Thomas, et al., "Ozonolysis of Phospholipid Double Bonds during Electrospray Ionization: A New Tool for Structure Determination", J. Am. Chem. Soc. (2006), p. 58-59, vol. 128, American Chemical Society.

Michael C.Homas, et al., "Elucidation of Double Bond Position in Unsaturated lipids by Ozone Electrospray Ionization Mass Spectrometry", Analytical Chemistry (Jul. 1, 2007), p. 5013-5022, vol. 79, No. 13, American Chemical Society.

Stephen J. Blanksby, et al., "Reactions of zone with unsaturated phosolipids in the gas phase: mechanisms of oxidative stress", 17$^{th}$ International Mass Spectrometry Conference, (Aug. 31, 2006).

Michael C.Thomas, "Ozonolysis of lipid double bonds: a comparison between insourse and in vacuo ozonolysis" Univeristy of Wollongong Annual Department of Chemistry Conference, (Oct. 23, 2006).

Michael C.Thomas, et al, "Ozonolysis of phospholipids double bonds: a comparison between in-source and in vacuo ozonolysis", 21$^{st}$ Conference of the Australian and New Zealand Society for Mass Spectrometry, (Jan. 23, 2007).

*Primary Examiner*—Robert Kim
*Assistant Examiner*—Johnnie L Smith
(74) *Attorney, Agent, or Firm*—Sughrue Mion, PLLC

(57) ABSTRACT

A mass spectrometric method for determining the position of unsaturation in a compound is disclosed.

11 Claims, 14 Drawing Sheets

METHOD FOR THE DETERMINATION OF THE POSITION OF UNSATURATION IN A COMPOUND

TECHNICAL FIELD

The present invention relates to a mass spectrometric method for determining the position of unsaturation in a compound.

BACKGROUND OF THE INVENTION

Mass spectrometry (MS) is a technique whereby the mass of individual molecules or compounds can be measured with extremely high accuracy. It is a ubiquitous technique with applications in many areas including sport, medicine, airport security and the food industry. Although tandem mass spectrometry (MS/MS) is one of the most powerful analytical tools available for the elucidation of molecular structure, and can identify the number of unsaturated bonds in a molecule, it often lacks the ability to locate the position of unsaturation within molecules. This can be a significant limitation given the variation in physical and chemical properties of a molecule that can arise as a result of variations in the position of unsaturation.

In recent years mass spectrometry has become arguably the most important tool in the quantification and structural characterisation of lipids within biological extracts. By utilizing electrospray ionization tandem mass spectrometry (ESI-MS/MS), the lipid class, carbon chain length and degree of unsaturation of fatty acid components of lipids can be determined. Unsaturated bond position however, has been largely ignored in this kind of analysis which belies the natural diversity in lipid biochemistry. This is of major importance since lipid isomers differing only by the positions of unsaturation can have distinct biological functions.

One method used to identify the position of unsaturation in intact lipids using mass spectrometry is the collision induced dissociation (CID) of carboxylate anions formed upon fragmentation of the parent phospholipid anion in an $MS^3$ experiment. Comparison of the resultant $MS^3$ spectrum with the MS/MS spectrum of the deprotonated free fatty acid can, in some instances, elucidate the double bond position in the bound fatty acid. In practice however, there are several disadvantages associated with such an experiment; (i) it requires an $MS^3$ capable mass spectrometer, (ii) the low energy CID of deprotonated fatty acids are often not structurally diagnostic, e.g., often only dehydration and/or decarboxylation is observed, and (iii) the alternative high energy CID can produce excessive fragmentation making for very complex interpretation in the absence of comparative standards.

The present inventors have previously demonstrated that in-source ozonolysis is an effective tool in determining the position of double bonds in purified lipids or very simple mixtures of mostly saturated lipids. However, the analysis of complex lipid mixtures, particularly those with a high degree of unsaturation, is insensitive and yields highly complex and structurally ambiguous data. The most significant limitation is that ozone induced dissociation of two ionized lipids of different mass can yield fragments of the same mass. Furthermore, low abundance ozone induced fragment ions can be obscured by unoxidised lipid ions.

There is therefore a need for an improved mass spectrometric method whereby the position(s) of unsaturation in a compound can be determined, that at least partially addresses the deficiencies associated with known methods.

SUMMARY OF THE INVENTION

In a first aspect, the present invention provides a method for determining the position of unsaturation in a compound comprising one or more unsaturated chains, the method comprising:

(i) ionizing the compound to provide ions;

(ii) selecting ions of a given mass-to-charge ratio;

(iii) allowing the selected ions to react with ozone to give ozone induced fragment ions;

(iv) mass analysis and detection of the ozone induced fragment ions formed in step (iii); and (v) determining the position of unsaturation in the compound based on the difference between the mass-to-charge ratio of the ions selected in step (ii), and the mass-to-charge ratio of one or more of the ozone induced fragment ions formed from the selected ions in step (iii).

The compound may be selected from the group consisting of: polymers, metabolites, lipids, fatty acids, drugs, biological extracts and natural products.

The compound may be present as part of a mixture of compounds.

The compound may be a lipid or a fatty acid.

The lipid may be a triacylglycerol, a diacylglycerol or a monoacylglycerol.

The compound may be present as part of a mixture of lipids.

The compound may be present as part of a mixture of phospholipids.

The compound may be present as part of a mixture of fatty acids.

The compound may be part of a biological extract.

The compound may be a phospholipid.

The unsaturation may be one or more carbon-carbon double bonds.

The one or more unsaturated chains may be one or more alkenyl chains, the alkenyl chains comprising either a single double bond or multiple double bonds.

The one or more unsaturated chains may be one or more alkenyl chains, the alkenyl chains comprising between 1 and 25, or between 1 and 20, or between 1 and 15, or between 1 and 10, or between 1 and 5 double bonds.

The one or more unsaturated chains may be one or more alkenyl chains, the alkenyl chains comprising either a single double bond or multiple double bonds, and where the alkenyl chains terminate with methyl or methylene groups.

The compound may comprise one or more alkenyl chains, the alkenyl chains comprising between 1 and 25, or between 1 and 20, or between 1 and 15, or between 1 and 10, or between 1 and 5 double bonds, and where the alkenyl chains terminate with methyl or methylene groups.

The compound may comprise one or more alkenyl chains, the alkenyl chains comprising between 1 and 25, or between 1 and 20, or between 1 and 15, or between 1 and 10, or between 1 and 5 double bonds, and where the alkenyl chains terminate with a methyl group.

The compound may be ionized by electrospray ionization (ESI), electron ionization (EI), chemical ionization (CI), matrix assisted laser desorption ionization (MALDI), atmospheric pressure chemical ionization (APCI), desorption electrospray ionization (DESI), direct analysis in real time (DART), fast atom bombardment (FAB) or thermospray.

The method may further comprise determining the stereochemistry of one or more carbon-carbon double bonds based on the relative abundance of the ozone induced fragment ions.

The selected ions may be allowed to react with ozone in, for example, an ion trap, an ion cyclotron resonance (ICR) mass spectrometer, a quadrupole, hexapole, or other multipole (usually acting as a collision cell), a flow tube (for example a selected ion flow tube), or a high pressure mass spectrometer.

Step (v) may comprise determining the position of unsaturation in the compound based on the mass-to-charge ratio of one or more ozone induced fragment ions, wherein the one or more ozone induced fragment ions comprises an aldehyde functional group, or wherein the one or more ozone induced fragment ions is a Criegee ion, or wherein the one or more ozone induced fragment ions are fragments of the fragment comprising an aldehyde functional group, or fragments of the Criegee ion.

The method may be used in conjunction with CID mass spectrometry.

In a second aspect, the present invention provides a method for determining the position(s) of one or more carbon-carbon double bond(s) in a compound comprising one or more unsubstituted alkenyl chains, the method comprising:

(i) ionizing the compound to provide ions;

(ii) selecting ions of a given mass-to-charge ratio;

(iii) allowing the selected ions to react with ozone to give ozone induced fragment ions;

(iv) mass analysis and detection of the ozone induced fragment ions formed in step (iii); and (v) determining the position(s) of the double bond(s) in the compound according to any one of the following formulae (I) to (V):

$$n = \frac{m/z(M) - m/z(\text{Criegee}) + 32 + 2b}{14} \quad \text{(I)}$$

$$n = \frac{m/z(M) - m/z(\text{aldehyde}) + 16 + 2b}{14} \quad \text{(II)}$$

$$n = \frac{m/z(M) - m/z(\text{Criegee} - H_2O) + 14 + 2b}{14} \quad \text{(III)}$$

$$n = \frac{m/z(M) - m/z(\text{Criegee} - NMe_3) - 27 + 2b}{14} \quad \text{(IV)}$$

$$n = \frac{m/z(M) - m/z(\text{aldehyde} - NMe_3) - 43 + 2b}{14} \quad \text{(V)}$$

wherein:

"n" is an integer representing the position of the carbon-carbon double bond as numbered from the carbon of the terminal methyl or methylene group of the alkenyl chain;

"M" refers to the ions selected in step (ii);

"aldehyde" refers to the ozone induced fragment ion comprising an aldehyde functional group as a result of ozone induced dissociation of M;

"Criegee" refers to the ozone induced fragment ion located 16 mass units above the mass of the aldehyde fragment ion as a result of ozone induced dissociation of M;

"Criegee-$H_2O$" refers to the secondary fragment formed from the Criegee ion resulting from loss of water (−18 Da);

"Criegee-$NMe_3$" refers to the secondary fragment formed from the Criegee ion in phosphocholine-containing compounds resulting from loss of trimethylamine (−59 Da);

"aldehyde-$NMe_3$" refers to the secondary fragment formed from the aldehyde ion in phosphocholine-containing compounds resulting from loss of trimethylamine (−59 Da); and, "b" is an integer representing the number of double bonds between the position of fragmentation and the carbon of the terminal methyl or methylene group of the alkenyl chain.

The compound may be a compound as defined in the first aspect.

The alkenyl chain(s) may comprise either a single double bond or multiple double bonds.

The alkenyl chain(s) may comprise either a single double bond or multiple double bonds, and may terminate with a methyl group.

The alkenyl chain(s) may comprise between 1 and 25, or between 1 and 20, or between 1 and 15, or between 1 and 10, or between 1 and 5 double bonds.

In a third aspect, the present invention provides a method for determining the position of a double bond in a compound of the general formula $M^1$-(CH═CH)-$M^2$, wherein $M^1$ and $M^2$ independently represent any organic residue, the method comprising:

(i) ionizing the compound to provide ions;

(ii) selecting ions of a given mass-to-charge ratio;

(iii) allowing the selected ions to react with ozone to give ozone induced fragment ions;

(iv) mass analysis and detection of the ozone induced fragment ions formed in step (iii); and (v) determining the position of the double bond in the compound based on the relative masses of $M^1$ and $M^2$.

Step (v) may be carried out as follows:

(a) determining the mass of $M^1$ by subtracting 29 Da from the observed mass of the ozone induced fragment ion comprising an aldehyde functional group; or (b) determining the mass of $M^1$ by subtracting 45 Da from the observed mass of the ozone induced fragment ion which is a Criegee ion;

(c) determining the mass of $M^2$ by solving the following formula for $M^2$: $M=M^1+M^2+C_2H_2$, wherein M is the mass of the ions selected in step (ii), and (d) assigning the position of the double bond based on the relative masses of $M^1$ and $M^2$.

In some embodiments, it may be necessary to determine the structure of the compound, with the exception of the double bond position, prior to performing the method of the first, second or third aspects.

The method of the first, second or third aspects may be used as the last step in a structural determination process, whereby all structural information is known about the compound, with the exception of the position(s) of the double bond(s).

In a fourth aspect, the present invention provides a system for determining the position(s) of unsaturation in a compound comprising one or more unsaturated chains, the system comprising:

(i) means for ionizing the compound to provide ions;

(ii) means for selecting ions of a given mass-to-charge ratio;

(iii) means for allowing the selected ions to react with ozone to give ozone induced fragment ions;

(iv) means for mass analysing and detecting the ozone induced fragment ions formed in step (iii); and (v) means for determining the position of unsaturation in the compound based on the difference between the mass-to-charge ratio of the ions selected in step (ii), and the mass-to-charge ratio of one or more of the ozone induced fragment ions formed from the selected ions in step (iii).

The means for ionizing the compound to provide ions may be selected from the group consisting of: electrospray ionization (ESI), electron ionization (EI), chemical ionization (CI), matrix assisted laser desorption ionization (MALDI), atmospheric pressure chemical ionization (APCI), desorption electrospray ionization (DESI), direct analysis in real time (DART), fast atom bombardment (FAB) and thermospray.

The means for selecting ions of a given mass-to-charge ratio may be an ion trap, an ion cyclotron resonance mass spectrometer, a quadrupole (or other multipole), a time-of-flight analyser, an ion mobility device, a sector field magnet or an electrostatic analyser.

The means for allowing the selected ions to react with ozone may be an ion trap, a collision cell, an ion cyclotron resonance mass spectrometer, an ion mobility device or a flow tube.

The means for mass analysing and detecting the ozone induced fragment ions may be an ion trap, an ion cyclotron resonance mass spectrometer, a quadrupole (or other multi-pole), a time-of-flight analyser, an ion-mobility device, an electrostatic trap, a sector field magnet or an electrostatic analyser.

Step (v) may be carried out as follows using a computer program. First, information in relation to selected molecular structural features of the compound obtained by other spectroscopic techniques (for example MS (such as HRMS or CID), NMR, IR, UV-VIS, etc.) is entered into the program. The program then utilises this information to calculate the molecular structure of the compound, with the exception of the position(s) of unsaturation. The program then receives data in relation to the ozone induced dissociation of a mass selected ion, and proceeds to calculate the position(s) of unsaturation based on the ozone induced dissociation data and the previously entered data.

The method described herein relies on ozone induced dissociation of mass-selected ions and may thus be referred to as “OzID”.

DEFINITIONS

In the context of this specification, the term “comprising” means “including principally, but not necessarily solely”. Furthermore, variations of the word “comprising”, such as “comprise” and “comprises”, have correspondingly varied meanings.

In the context of this specification, the term “neutral loss” or “neutral gain” is understood to mean the difference in mass-to-charge ratio between the mass selected ions and the ozone induced fragment ions.

In the context of this specification, the term “alkenyl” is understood to mean any hydrocarbon chain comprising one or more carbon-carbon double bonds.

In the context of this specification, the term “unsubstituted alkenyl chain” is understood to mean any hydrocarbon chain comprising one or more carbon-carbon double bonds, wherein no additional functional groups are present within, or attached to, the hydrocarbon chain.

In the context of the present specification, the term “ozone induced fragment ions” is understood to mean ions obtained following reaction of mass selected ions with ozone.

BRIEF DESCRIPTION OF THE FIGURES

A preferred embodiment of the present invention will now be described, by way of example only, with reference to the accompanying drawings wherein.

12B shows a spectrum following ozone induced dissociation of the [GPCho(9E-18:1/9E-18:1)+H]$^+$.

DETAILED DESCRIPTION OF THE INVENTION

The inventors have developed a method that allows unambiguous determination of the position(s) of unsaturation in a compound or compounds. The method is applicable to any unsaturated compounds, or compounds having functional groups that react with ozone, for example fatty acids, lipids, small molecule drugs, polymers or natural products.

The method is advantageous where it is desired to determine the position of unsaturation in one or more compounds in a complex mixture. The method provides molecular structure information that is not available from traditional collision induced dissociation (CID). Unlike existing methods, the method of the present invention is applicable to the analysis of individual lipids isolated only by mass-selection of individual ions following electrospray ionization of unfractionated lipid extracts.

Figure 1:
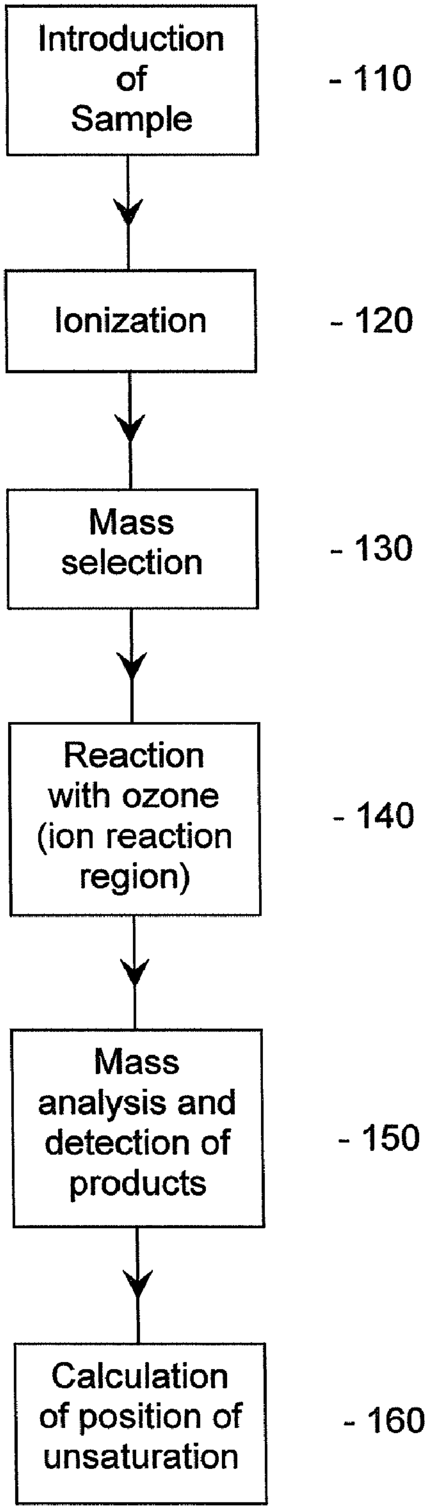
FIG. 1 shows a simple scheme setting out the steps involved in determining the position of unsaturation in a compound in accordance with an embodiment of the invention.

FIG. 1 depicts the steps involved in an embodiment of the method of the present invention. First, a sample to be analysed (for example, a mixture of lipids or fatty acids) is introduced into the mass spectrometer (110). Positive or negative ions of the sample are generated in the source, by, for example electrospray, electron impact or chemical ionization, or any other method that produces ions of the sample (120). The ions may be [M+H]$^+$, [M+Li]$^+$, [M+Na]$^+$, [M−H]$^-$, or any other suitable ions. Ions having a single mass-to-charge ratio are mass selected (130) by, for example, a quadrupole. The ions of a single mass-to-charge ratio are then reacted with ozone in an ion reaction region (140). Where the mass analyser is capable of facilitating reaction of the selected ions with ozone (e.g. a quadrupole ion trap), the ions may be both mass selected and reacted with ozone in this component of the mass spectrometer. Where a separate mass analyser, such as a quadrupole which precedes the ion reaction region is employed, the ions can be mass selected by the quadrupole, and then conveyed to the ion reaction region (e.g. an ion trap) where reaction with ozone takes place. The ozone may be introduced into the reaction chamber by itself, or with any other unreactive buffer gas such as oxygen, helium, nitrogen or argon.

The fragment ions resulting from the reaction of the mass selected ions with ozone are mass analysed and detected (150), and a spectrum is obtained. The position of unsaturation is then determined (160) based on the difference between the mass-to-charge ratio of the ions selected in (130) above, and the mass-to-charge ratio of one or more of the ozone induced fragment ions. Determination of the position of unsaturation based on the ozone induced fragment ions is described in detail below.

By performing the ozonolysis reaction on mass-selected ions, it is now possible to unambiguously determine the location of the position of unsaturation in compounds present in complex mixtures. This is based on the fact that the mass-to-charge ratios of the chemically induced fragment ions are diagnostic of the position of unsaturation within the precursor ion. As an example, if it is desired to determine the double bond position(s) of a compound of interest having a mass-to-charge ratio of 850, then in the method of the invention this ion may be mass-selected following ionization, reacted with ozone, and the double bond positions determined based on the ozone induced fragment ions obtained. Because the ozonolysis reaction occurs with ions of a single mass-to-charge ratio, the resulting spectra are relatively simple, unambiguous and interference from fragments resulting from the reaction of other compounds having a mass-to-charge ratio of other than 850 with ozone, are avoided. In addition, by harnessing the capability of the mass spectrometer to mass select or isolate a compound of interest, the need for time consuming chromatographic separation may, in some cases, be obviated.

The method can be performed using any type of trapping mass spectrometer (e.g., ion-trap or ion cyclotron resonance) or any tandem mass spectrometer (e.g., quadrupole-time of flight, triple quadrupole or selected ion flow tube) that can provide sufficient residence time for ions to undergo reaction with ozone. In one embodiment, the method of the invention may be performed on a modified ThermoFinnigan LTQ ion-trap mass spectrometer.

Reaction of Selected Ions with Ozone

In order to facilitate the reaction of the mass-selected ions with ozone, modifications to a typical trapping mass spectrometer (for example, a ThermoFinnigan LTQ ion-trap mass spectrometer) may be required. In an embodiment of the invention, this is achieved by connecting a reservoir of ozone directly to an inert gas line, wherein the inert gas line is in communication with, for example, a reaction chamber as depicted in FIG. 2.

Figure 2:
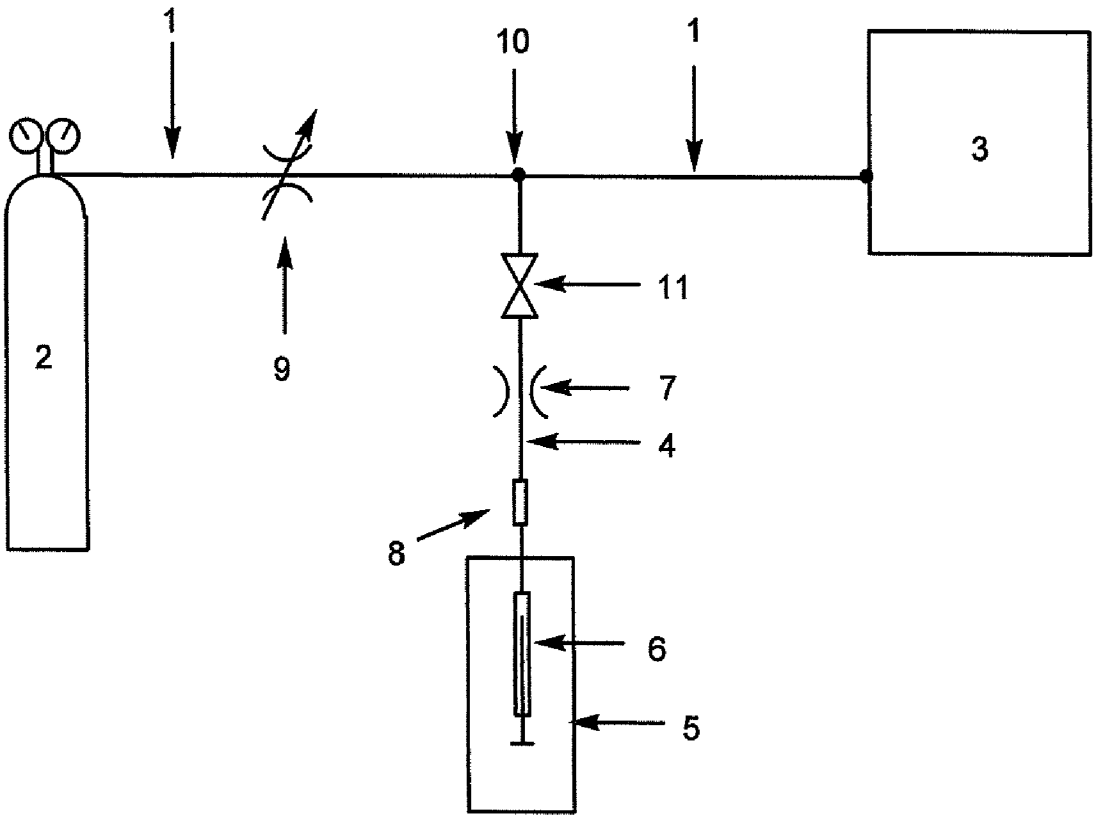
FIG. 2 shows an example of a modified mass spectrometer that may be used to carry out the reaction of mass-selected ions with ozone.

Referring to FIG. 2, flow line 1 facilitates the transfer of inert gas from inert gas source 2 to reaction chamber 3 (which may be an ion trap), via metering flow valve 9. The inert gas may be, for example, helium, nitrogen or argon, or any other gas that does not react with ozone. At a section of flow line 1 between the inert gas source 2 and the reaction chamber 3, ozone is introduced via flow line 4, through a valve 11 and T-junction 10. The ozone is delivered to flow line 4 using a syringe pump 5 and a gas tight syringe 6, the gas tight syringe comprising ozone. Flow line 4 also comprises a restrictor 7 and union 8, which couples the syringe to flow line 4. The restrictor 7 controls the flow of ozone, and may be a PEEKsil® tubing restrictor (100 mm L×1/16" OD×0.025 mm ID) (SGE). In one embodiment, flow line 4 comprises PEEKsil® tubing, however alternative tubing may be used as long as such tubing does not react with ozone. The ozone may be produced externally using a commercial high concentration ozone generator, for example a HC-30 model, available from Ozone Solutions, Sioux Center, Iowa, USA.

In use, inert gas source 2 is activated to introduce inert gas into flow line 1, and the flow rate of inert gas may be set at approximately 0.1-2 mL/min using metering flow valve 9. The gas tight syringe 6 is charged with externally prepared ozone and placed in syringe pump 5. When the syringe pump 5 is activated, ozone exits the gas tight syringe 6, and enters flow line 4. Once in flow line 4, the ozone travels through union 8 to restrictor 7. Restrictor 7 may control the flow rate of ozone to about 10-25 μL/min. After exiting restrictor 7, the ozone travels to T-junction 10 via flow valve 11. At T-junction 10, the ozone enters flow line 1, where it mixes with the inert gas. The inert gas/ozone mixture travels along flow line 1 to reaction chamber 3, where the ozone reacts with the selected ions.

In an alternative embodiment of the invention, ozone may be delivered to reaction chamber 3 in the absence of the inert gas.

Determination of the Position of Unsaturation Based on Ozone Induced Fragment Ions The position of unsaturation in an unsaturated compound may be determined based on the mass-to-charge ratios of the fragment ions obtained following reaction of mass-selected ions with ozone. The fragment ions obtained are characteristic of the position of unsaturation.

Scheme 1 below depicts an example of the reaction of ozone with a phospholipid ion (GPCho(16:0/9Z-18:1) where the m/z is 782, and the products obtained therefrom.

Scheme 1: Reaction of a phospholipid with ozone and the products obtained.
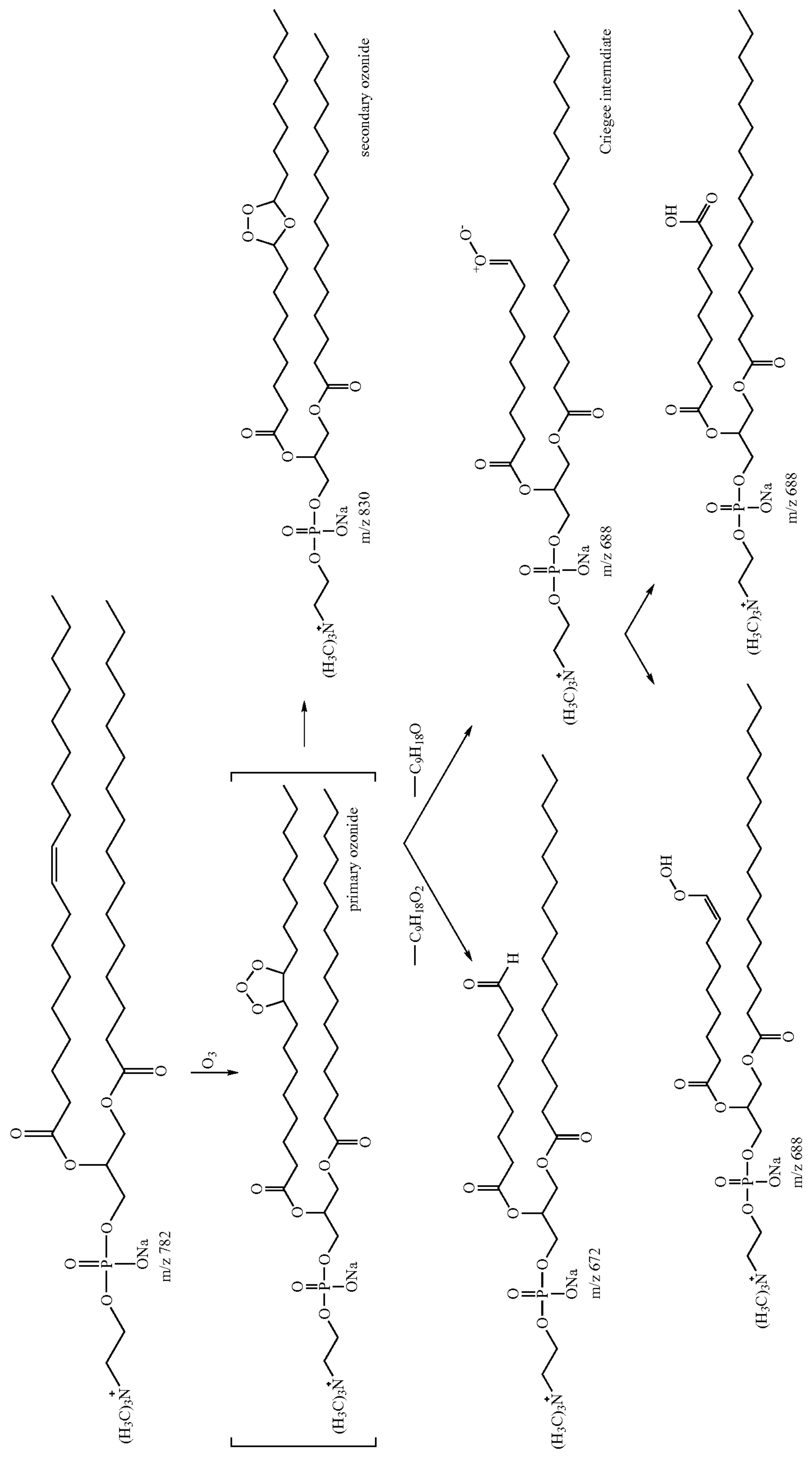

Referring to Scheme 1, ozone adds to the double bond of the phospholipid leading to the formation of a primary ozonide. The primary ozonide is unstable and rapidly dissociates to form an aldehyde and a carbonyl oxide. The carbonyl oxide is unstable, and likely rearranges to produce either a vinyl hydroperoxide or a carboxylic acid. The fragment comprising the carbonyl oxide functional group (or alternate structure) is referred to as a "Criegee ion". An additional reaction product that may be obtained is a secondary ozonide, which has a molecular weight greater than that of the selected ion.

In the case of lipids for example, the position of unsaturation may be determined as follows.

A mass spectrum is obtained of the sample under analysis. The observed mass of the ions of interest provides an initial indication of the identity of the lipid by comparison with standard tables (Han, X. and Gross, R. W., "*Shotgun Lipidomics: Electrospray ionization mass spectrometric analysis and quantitation of cellular lipidomes directly from crude extracts of biological samples*", Mass Spectrometry Reviews (2005) 24: 367-412).

CID spectra are then obtained. The identity of the head group, the number of carbons, and the number of double bonds in the fatty acid fragments are determined by established methods (Pulfer, M. and Murphy, R. C., "*Electrospray mass spectrometry of phospholipids*", Mass Spectrometry Reviews (2003) 22(5): 332-364).

The method of the invention is then performed on the ions of interest, and the pair(s) of ions corresponding to the aldehyde and Criegee products resulting from the reaction of ozone with the double bond(s) are identified (these ions differ by m/z 16).

The position(s) of the double bond(s) may then be determined using the formula (I) or the formula (II) for each double bond:

$$n = \frac{m/z(M) - m/z(\text{Criegee}) + 32 + 2b}{14} \quad \text{(I)}$$

$$n = \frac{m/z(M) - m/z(\text{aldehyde}) + 16 + 2b}{14} \quad \text{(II)}$$

wherein:

"n" is an integer representing the position of the carbon-carbon double bond as numbered from the carbon of the terminal methyl or methylene group of the alkenyl chain;

"M" refers to ions selected in step (ii);

"aldehyde" refers to the ozone induced fragment ion comprising an aldehyde functional group as a result of ozone induced dissociation of M;

"Criegee" refers to the ozone induced fragment ion located 16 mass units above the mass of the aldehyde fragment ion as a result of ozone induced dissociation of M; and "b" is an integer representing the number of double bonds between the position of fragmentation and the carbon of the terminal methyl or methylene group of the alkenyl chain.

Formulae (I) and (II) are applicable to compounds having both monounsaturated and polyunsaturated hydrocarbon chains, for example lipids. The formulae are applied to lipids as a working example only in the following paragraphs. It is to be understood that formulae (I) and (II) can be applied to any unsaturated compound that comprises one or more unsubstituted alkenyl chains, the alkenyl chains comprising either a single double bond or multiple double bonds, and where the alkenyl chain(s) terminate with a methyl or methylene group.

In solving formulae (I) and (II) for n, an iterative process may be used whereby b is set equal to 0, 1, 2, 3 etc., until an integer value for n is obtained. This integer value represents the double bond position, and the integer value obtained plus one provides the total number of double bonds in the alkenyl chain. Such an iterative process may be used where the number of double bonds in an alkenyl chain is unknown, or where it is known that an alkenyl chain has more than one double bond present.

Where it has already been determined that the unsaturated compound comprises a single double bond only, b is set simply set to zero and n determined accordingly based on the difference between m/z(M), and m/z of the aldehyde or Criegee ion fragments. An example of the application of formulae (I) and (II) to a monounsaturated compound is given below.

In the case of the phospholipid species given above in Scheme 1 (GPCho(16:0/9Z-18:1) for example, using standard CID experiments (not shown), it is established that the head group is phosphatidylcholine (PC) and that the fatty acid chains comprise 18 and 16 carbons, and that the 18 carbon chain comprises a single double bond. Applying formula (I), n=(782−688+32+0)/14=9. Therefore, the double bond in the 18 carbon chain resides at position 9 of the alkenyl chain from the methyl terminus. Applying formula (II), n=(782−672+16+0)/14=9, thereby confirming the double bond resides at position 9.

An example of the application of formulae (I) and (II) to a compound comprising a polyunsaturated hydrocarbon chain is given below.

The compound shown in Example 9 has four double bonds in one of the hydrocarbon chains. The compound displays an $[M-H]^-$ ion at 885, and shows four sets of fragment ions (see FIG. 10B). Substitution of the ozone induced aldehyde fragment found at m/z 697 (aldehyde) into formula (II), and setting b to equal 0 gives the following n value:

$$n=(885-697+16+0)/14=14.6$$

Because 14.6 is not an integer, b is set to 1 in formula (II), which gives the following n value:

$$n=(885-697+16+2)/14=14.7$$

Because 14.7 is not an integer, b is set to 2 in formula (II), which gives the following n value:

$$n=(885-697+16+4)/14=14.9$$

Because 14.9 is not an integer, b is set to 3 in formula (II), which gives the following n value:

$$n=(885-697+16+6)/14=15$$

Because an integer for n is returned for b=3, it can be deduced that there is a double bond at position 15, and that there are 3 additional double bonds in the chain, all of which fall between position 15 and the terminus of the alkenyl chain.

A similar approach can be applied using formula (I) and the corresponding Criegee ion located at m/z 713. In addition, any of the other pairs of fragment ions indicated by ■ and ● in FIG. 10B may be used in conjunction with formulae (I) or (II) to determine the location of the additional three double bonds.

In the example given in Scheme 1 above, the neutral loss of 110 Da is characteristic of the aldehyde ion and the neutral loss of 94 Da is characteristic of the Criegee ion obtained from the ozone induced fragmentation of a monounsaturated phospholipid having a double bond at the 9 position of the alkenyl chain from the methyl terminus. If the double bond was located at position 10 of the alkenyl chain from the methyl terminus, the neutral loss characteristic of the aldehyde ion would be 124 Da, and the neutral loss characteristic of the Criegee ion would be 108 Da. It is noted that the neutral losses differ by +14 Da when the position of the double bond moves one carbon further from the methyl terminus.

Table 1 below has been prepared to serve as a quick reference guide to assigning the double bond position (from the terminal methyl or methylene carbon) when interpreting fragments produced by reaction of particular mass-selected ions with ozone. Table 1 can be applied to any unsaturated compound of interest that comprises one or more unsubstituted alkenyl groups, the alkenyl group(s) comprising either a single double bond or multiple double bonds, and where the alkenyl group(s) terminate(s) with a methyl or methylene group.

It is noted that where a double bond is located at position 1 of an unsaturated chain, the aldehyde fragment and Criegee ion will have a mass greater than the mass-selected ion, leading to a neutral gain in relation to the ozone induced fragment ions, rather than a neutral loss. The same situation applies to the Criegee ion where the double bond is located at position 2 of the unsaturated chain.

An example of the use of the information in Table 1 is as follows. A phospholipid ion having a mass-to-charge ratio of 978 is selected, and subsequently reacted with ozone. The ozone induced fragment ions are observed at m/z 812 and 828. These ions correspond to neutral losses of 96 and 80 Da respectively. Reference to Table 1 shows that such neutral losses are characteristic of a single double bond at position 8 of the alkenyl chain from the methyl terminus.

TABLE 1

Neutral gains/losses expected from several double bond positions in compounds comprising alkenyl chains*

| Unsaturated bond position in alkenyl chain (determined from terminal carbon ($CH_3$))# | Neutral gains (+)/ losses (−) observed | |
|---|---|---|
| | Aldehyde | Criegee ion |
| 1 | +2 | +18 |
| 2 | −12 | +4 |
| 3 | −26 | −10 |
| 4 | −40 | −24 |
| 5 | −54 | −38 |
| 6 | −68 | −52 |
| 7 | −82 | −66 |
| 8 | −96 | −80 |
| 9 | −110 | −94 |
| 10 | −124 | −108 |
| 11 | −138 | −122 |
| 12 | −152 | −136 |
| 13 | −166 | −150 |
| 14 | −180 | −164 |
| 15^ | −194 | −178 |

*In polyunsaturated chains when the neutral loss is unsaturated, 2 Da is subtracted from the neutral losses for each double bond.
#or determined from (=$CH_2$) terminal carbon where a double bond resides at position 1 of the alkenyl chain.
^The table can be easily extrapolated beyond 15 by subtracting 14 for each additional carbon position in the alkenyl chain.

Other secondary fragments may be observed following ozone induced dissociation of particular compounds. These secondary fragments may also be diagnostic of the position(s) of unsaturation, and could therefore be useful in the method of the invention.

Some lipid anions may display a minor ion resulting from a neutral loss of water from the Criegee ion. An example of this can be seen in FIG. 5 by reference to the ion located at m/z 661. Formula (III) below may therefore be solved for n to calculate the position of unsaturation based on an ion resulting from a neutral loss of water from a Criegee ion:

$$n = \frac{m/z(M) - m/z(\text{Criegee} - H_2O) + 14 + 2b}{14} \quad \text{(III)}$$

wherein: n, m/z, M, b and Criegee are as defined in formula (I).

Figure 5:
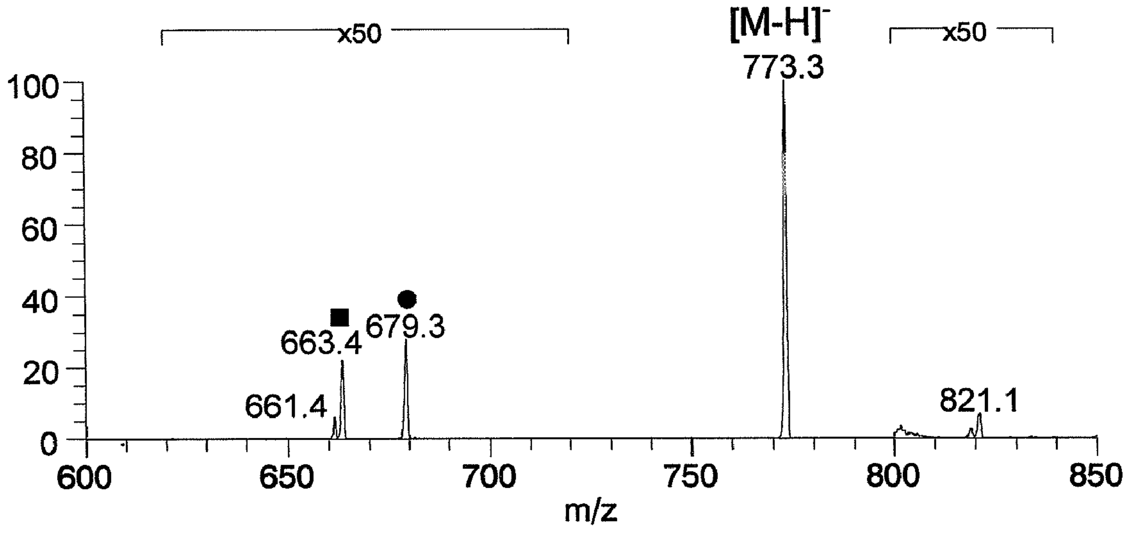
FIG. 5 shows the mass spectrum obtained following reaction of ozone with the $[M-H]^-$ ion of GPGro(9Z-18:1/9Z-18:1). The precursor ion was generated by electrospray ionization of a 1 μM methanolic solution of GPGro(9Z-18:1/9Z-18:1). The pair of ions resulting from ozonolysis of the double bond are labelled with ■ and ● indicating aldehyde and Criegee ions, respectively.

In the context of FIG. 5, formula (III) may be solved as follows:

$$n=(773-661+14+0)/14=9$$

Therefore, the double bonds are located at position 9.

Trimethylamine loss from Criegee ions and aldehyde ions of sodiated and lithiated phosphocholine-containing lipids may also be observed. Formula (IV) may be used to calculate the position of unsaturation based on an ion resulting from trimethylamine loss from a Criegee ion:

$$n = \frac{m/z(M) - m/z(\text{Criegee} - NMe_3) - 27 + 2b}{14} \quad \text{(IV)}$$

wherein: n, m/z, M, b and Criegee are as defined in formula (I).

An example of the use of formula (IV) in determining double bond position based on an ion corresponding to trimethylamine loss from a Criegee ion is given below in relation to FIG. 3. In the spectrum shown in FIG. 3, the ion located at m/z 629 corresponds to loss of trimethylamine from the Criegee ion. Formula (IV) may be solved for n as follows:

$$n=(782-629-27+0)/14=9$$

The double bond is therefore located at position 9.

Formula (V) may be used to calculate the position of unsaturation based on an ion resulting from trimethylamine loss from an aldehyde ion:

$$n = \frac{m/z(M) - m/z(\text{aldehyde} - NMe_3) - 43 + 2b}{14} \quad \text{(V)}$$

wherein: n, m/z, M, b and aldehyde are as defined in formula (II).

An example of the use of formula (V) in determining double bond position based on an ion corresponding to trimethylamine loss from an aldehyde ion is given below in connection with FIG. 3. In the spectrum shown in FIG. 3, an ion is located at m/z 613 corresponding to loss of trimethylamine from the aldehyde ion. Formula (V) may be solved for n as follows:

$$n=(782-613-43+0)/14=9$$

The double bond is therefore located at position 9.

Scheme 2 below presents a general scheme for interpretation of fragment ions obtained following the reaction of any mass-selected ions comprising carbon-carbon double bond(s) with ozone, in relation to determining the position(s) of the double bond(s). As set out below, Scheme 2 can be used to determine the position(s) of the double bond(s) in any compound comprising carbon-carbon double bond(s), based on the number of mass units calculated to be present on each side of the double bond(s).

Scheme 2: General scheme applicable to any unsaturated compound comprising carbon-carbon double bonds, detailing the fragments obtained following reaction of mass-selected ions with ozone, and the determination of double bond position based on the mass of fragments on each side of the double bond.

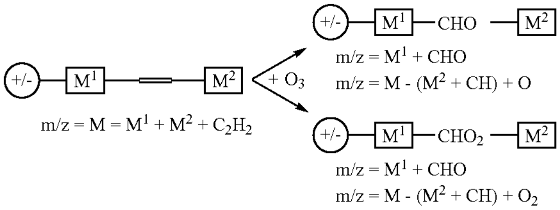

Referring to Scheme 2, the mass of the mass-selected ion (M) can be considered as the sum of: (i) the mass of the double bond itself consisting of 2 carbons and 2 hydrogens (2×12+2×1=26 Da), (ii) the mass of the molecule on the charged side of the double bond ($M^1$), and (iii) the mass of the molecule on the uncharged side of the double bond, ($M^2$). Therefore, $M=M^1+M^2+26$ Da.

The molecule may be ionized either as a positive ion or a negative ion. Measurement of the mass-to-charge ratio of the molecular ion by traditional mass spectrometry provides the molecular mass M. When applying the method of the invention, the ion is mass-selected and allowed to react with ozone to form the two fragment ions shown in Scheme 2. The mass-to-charge ratio of these ions appear at $M^1$+CHO (or $M^1$+29 Da) and $M^1+CHO_2$ (or $M^1$+45 Da). $M^1$ can therefore be easily determined. By knowing the molecular mass of M and also the value of $M^1$, one can also calculate $M^2$. With knowledge of the masses M, $M^1$ and $M^2$, the position of the double bond can be precisely located within the compound based on the number of mass units located on either side of the double bond. Those skilled in the art will realise that any mass gain or loss in the ionisation process, or decrease in m/z through increased charge, can be reflected in the formula depicted in Scheme 2 if necessary.

An example of the application of the general method depicted in Scheme 2 is set out below in Schemes 3 and 4.

Reference to Scheme 3 shows fragment ions obtained following reaction of a phospholipid with ozone. The aldehyde fragment ion was observed at m/z 650, and therefore $M^1$+CHO=650. $M^1$ is therefore determined to be 621. The Criegee ion was observed at m/z 666, and therefore $M^1+CHO_2=666$. $M^1$ is therefore confirmed to be 621. Knowing M and $M_1$, $M_2$ can be calculated from the following formula: $m/z=M=M^1+M^2+C_2H_2$. Solving for $M^2$ provides $M^2=113$.

Therefore, based on the above calculations there are 621 mass units on one side of the double bond, and 113 mass units on the other side of the double bond. This uniquely defines the position of the double bond in the compound.

Scheme 3: Determination of double bond position in an unsaturated compound based on the mass of fragments on each of the double bond, as calculated from fragments obtained following ozone induced dissociation of a mass-selected ion.
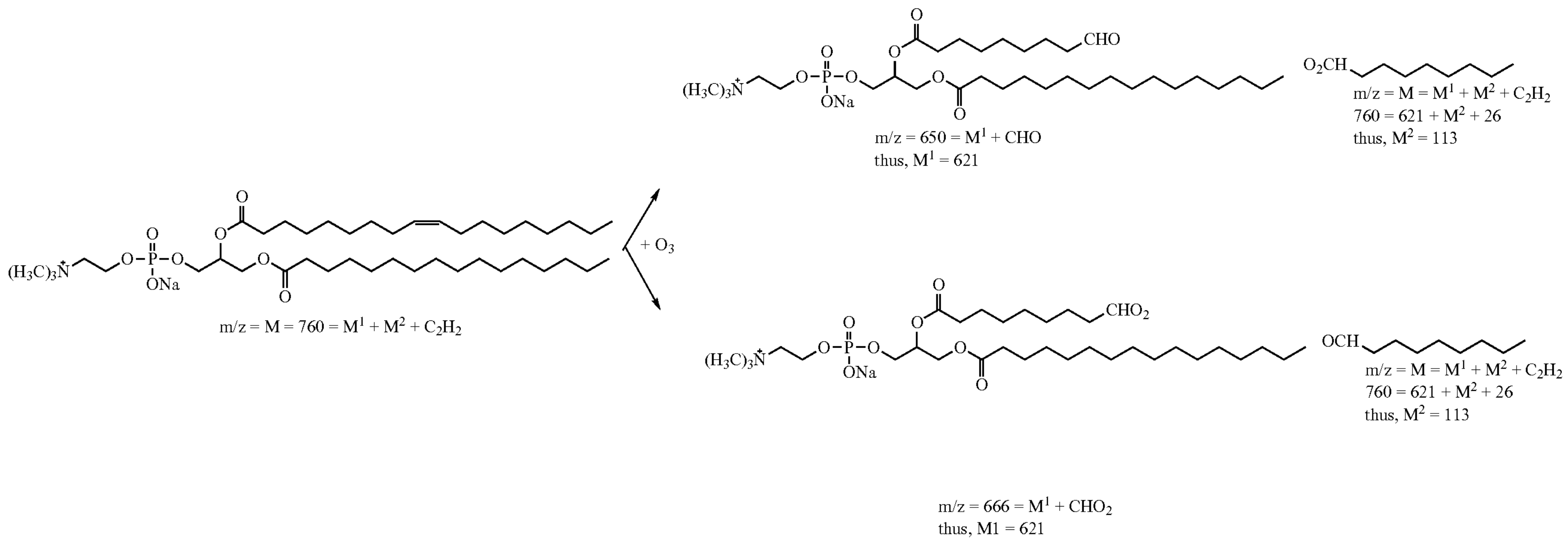

Reference to Scheme 4 shows fragments following reaction of the compound A with ozone. The aldehyde fragment was observed at m/z 260, and therefore $M^1$+CHO=260. $M^1$ is therefore determined to be 231. The Criegee ion was observed at m/z 276, and therefore $M^1+CHO_2$=276. $M^1$ is therefore confirmed to be 231. Knowing M and $M_1$, $M_2$ can be calculated from the following formula: m/z=M=$M^1+M^2+C_2H_2$. Solving for $M^2$ provides $M^2$=133.

Therefore, based on the above calculations, there are 231 mass units on one side of the double bond, and 133 mass units on the other side of the double bond. This uniquely defines the position of the double bond in the compound, in that the $M^1$ fragment is $PhCH(CH_3)CH_2CH_2$, and the $M^2$ fragment $C_6H_5NC(O)(CH_2)_8CH_2$, meaning that the double bond is located at position 4 in relation to the phenyl group.

with alternative spectroscopic techniques (and the uses thereof) that may be employed depending on the compound(s) of interest.

In one embodiment, the method of the invention may be used in series with CID experiments. For example, a CID spectrum of a given mass-selected ion may be obtained. A fragment ion identified in the CID spectrum may then be mass-selected and allowed to react with ozone, thereby allowing determination of the position of unsaturation in the selected fragment ion (see Example 10 below). Alternatively, CID spectra may be used in parallel with the method of the invention in order to determine other related structural information on a selected ion such as, for example, the identity of headgroups and fatty acyl chains in phospholipids.

Scheme 4: Determination of double bond position in an unsaturated compound based on the mass of fragments on each side of the double bond, as calculated from fragments obtained following ozone induced dissociation of a mass-selected ion.

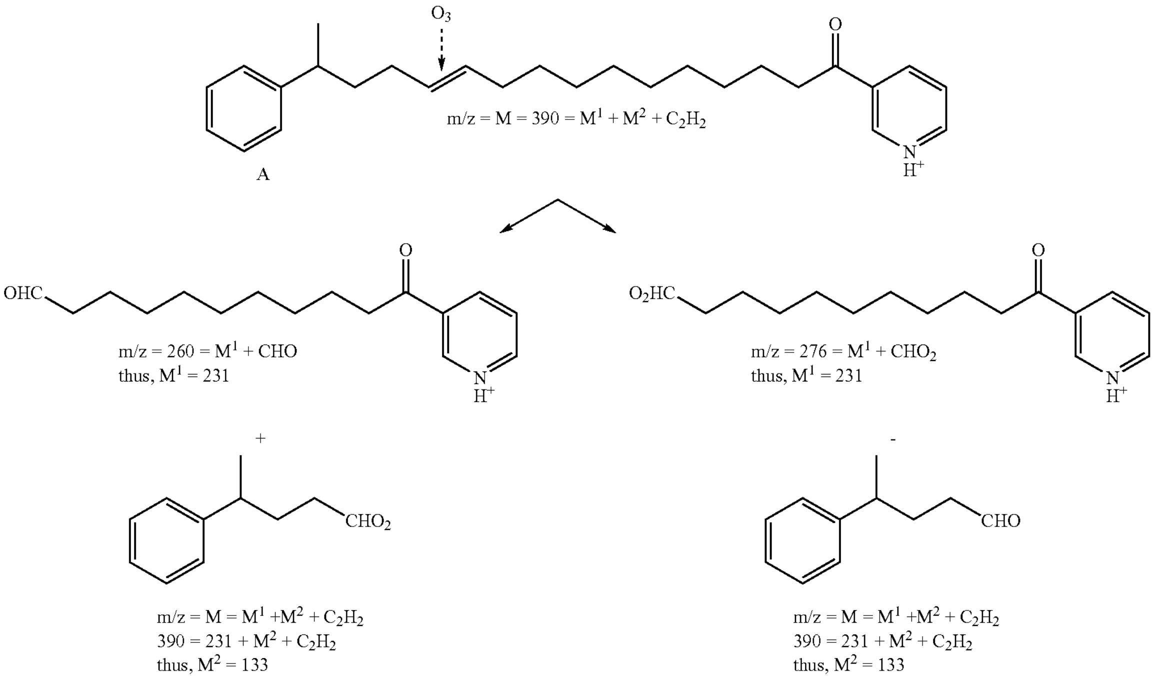

Figure 12A:
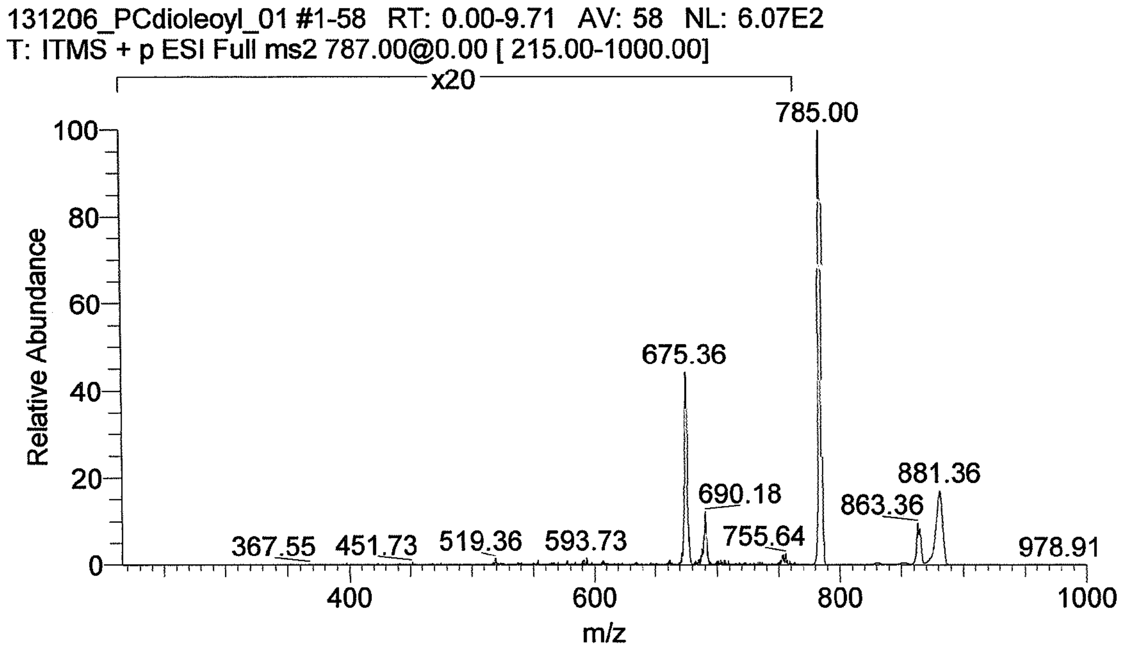
FIG. 12A shows a spectrum following ozone induced dissociation of the $[GPCho(9Z-18:1/9Z-18:1)+H]^+$ ion. FIG.
Figure 12B:
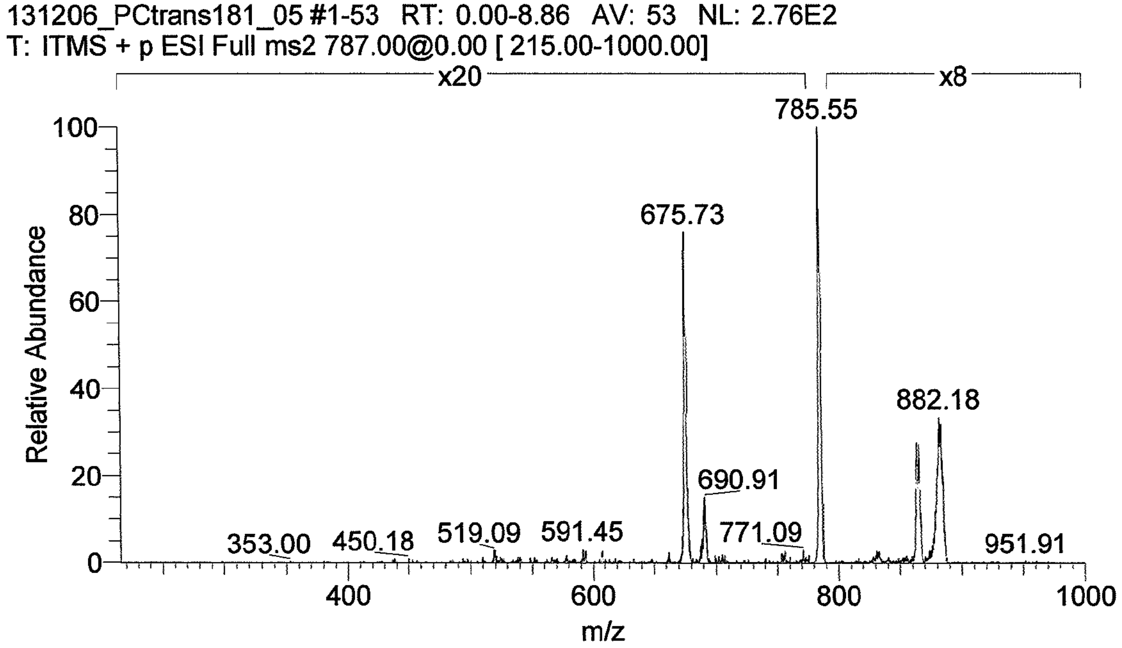

The method of the invention may also include determining the stereochemistry of double bonds based on the relative abundance of the ozone induced fragment ions. Reference to FIG. 12 shows that the ozone induced fragment ions (located at m/z 675 and 691) of the trans (E) isomer (FIG. 12B), are approximately 1.5 times as abundant as those of the cis (Z) isomer (FIG. 12A). Accordingly, the method of the invention may include determining the position of a double bond, and also its stereochemistry, based on the m/z and also the relative abundance of the ozone induced fragment ions.

Depending on the nature, environment and type of the compound(s) for which it is desired to determine the position of unsaturation, it may be necessary to first determine other information in relation to molecular structure of the compound(s) by other spectroscopic techniques (for example MS (such as HRMS and CID), NMR, IR, UV-VIS, etc.), prior to employing the method of the invention to determine the position of unsaturation. Those skilled in the art will be familiar The method of the invention may be used as the last step in a structural determination process, whereby all structural information is known about the molecule, with the exception of the position(s) of unsaturation.

The present invention also relates to a system that may be used to carry out the method of the invention. The system comprises:

(i) means for ionizing the compound to provide ions;

(ii) means for selecting ions of a given mass-to-charge ratio;

(iii) means for allowing the selected ions to react with ozone to give ozone induced fragment ions;

(iv) means for mass analysing and detecting the ozone induced fragment ions formed in step (iii); and (v) means for determining the position of unsaturation in the compound based on the difference between the mass-to-charge ratio of the ions selected in step (ii), and the mass-to-charge ratio of one or more of the ozone induced fragment ions formed from the selected ions in step (iii).

The means for ionizing the compound to provide ions may be selected from the group consisting of: electrospray ionization (ESI), electron ionization (EI), chemical ionization (CI), matrix assisted laser desorption ionization (MALDI), atmospheric pressure chemical ionization (APCI), desorption electrospray ionization (DESI), direct analysis in real time (DART), fast atom bombardment (FAB) and thermospray. Those skilled in the art will realise that other applicable means of ionisation may be employed in addition to, or as alternative to those listed above.

The means for selecting ions of a given mass-to-charge ratio may be an ion trap, an ion cyclotron resonance mass spectrometer, a quadrupole (or other multipole), a time-of-flight analyser, an ion mobility device, a sector field magnet, an electrostatic analyser, or any other suitable means that allows separation of ions based on their mass-to-charge ratios.

The means for allowing the selected ions to react with ozone may be an ion trap, a collision cell, an ion cyclotron resonance mass spectrometer, an ion mobility device or a flow tube.

The means for mass analysing and detecting the ozone induced fragment ions may be an ion trap, an ion cyclotron resonance mass spectrometer, a quadrupole (or other multipole), a time-of-flight analyser, an ion-mobility device, an electrostatic trap, a sector field magnet or an electrostatic analyser.

The means for selecting ions of a given mass-to-charge ratio may be a computer program. For example, information in relation to selected molecular structural features of the compound obtained by other spectroscopic techniques (for example MS (such as HRMS or CID), NMR, IR, UV-VIS, etc.) is entered into the program. The program then utilises this information to calculate the molecular structure of the compound, with the exception of the position(s) of unsaturation. The program then receives data in relation to the ozone induced dissociation of a mass selected ion, and proceeds to calculate the position(s) of unsaturation based on the ozone induced dissociation data and the previously entered data.

The method of the invention may find application in any area where molecular structure is required to be determined. Possible applications include:

- Metabolimics including lipidomics
- Food testing (double bond position and stereochemistry in fats and oils, e.g., quantitation of ω-3 lipids in margarine)
- Drug discovery, including natural products
- Disease diagnosis (for example, medical screening for inborn errors of metabolism)
- Structure elucidation in natural products
- Forensics
- Homeland security
- Proteomics
- Basic research, e.g.;
  - The method may prove useful as a probe of gas phase protein structure through selective oxidation of exposed sulfur-bearing amino acid residues (e.g., cysteine and methionine).

In addition to the above, given the relative simplicity of data interpretation and the ability to carry out de novo structure elucidation (i.e., without requiring authentic standards) the method of the present invention may be a useful adjunct to the evolving field of computer-based lipid identification.

The present invention will now be described with reference to specific examples, which should not be construed as in any way limiting the scope of the invention.

EXAMPLES

Example 1

General procedures for performing the method in Examples 2 et seq.

1. Materials and Sample Preparation

All synthetic phospholipid standards were purchased from Avanti Polar Lipids, Inc. (Alabaster, Ala.) and were used without further purification. The triacylglycerol standard TG(16:0/9Z-18:1/16:0) was purchased from Sigm-Aldrich. HPLC grade methanol and AR grade chloroform were purchased from Crown Scientific (Sydney, Australia). Sodium acetate was purchased from APS Chemicals (Sydney, Australia). Industrial grade compressed oxygen (purity 99.5%) and ultra high purity helium were obtained from BOC gases (Cringila, Australia). Standard solutions of phospholipids were prepared in methanol at concentrations of 1 to 10 μM. To aid the formation of sodium adducts 100 to 200 μM sodium acetate was added. Cow kidney was collected from the Wollondilly Abattoir and the phospholipids extracted by homogenisation with chloroform-methanol (2:1 v/v with 0.01% butylated hydroxytoluene). Normal human lenses were obtained from the Save Sight Institute (Sydney, Australia) and human cataractous lenses from the K. T. Sheth Eye Hospital (Rajkot, India). Phospholipids were extracted with chloroform-methanol (2:1 v/v with 0.01% butylated hydroxytoluene) after homogenisation under liquid nitrogen. Phospholipid extracts were made to approximately 40 μM in 2:1 methanol-chloroform for mass spectrometric analysis. Sodium adducts were observed under standard ESI conditions and could be further enhanced by the addition of 200 μM sodium acetate. Pure Spanish olive oil (Always Fresh) was obtained and diluted to approximately 2 mg/mL in methanol with 100 μM sodium acetate for mass spectrometric analysis.

2. Ozone Generation

A HC-30 ozone generator (Ozone Solutions, Sioux Center, Iowa, USA) was used for the production of ozone. Oxygen pressure was set to 20 psi and the ozone generator set to a power output of 68 (arbitrary units). To produce high concentration ozone, the oxygen flow rate was set at 400-500 mL/min for 20-30 minutes before the flow rate was decreased to between 30-40 mL/min for several minutes prior to ozone collection. The resulting ozone/oxygen mixture (12% v/v by titrimetric analysis) was collected in a 10 mL disposable plastic syringe (Livingstone). Warning: Ozone is a toxic gas and was produced in a fumecupboard. Excess ozone was destroyed by bubbling through an aqueous solution of sodium thiosulfate, sodium iodide and vitex indicator. Only ozone compatible materials were used. Rubber is not suitable.

3. Instrumentation and Ozone Delivery

OzID experiments were performed using a modified ThermoFinnigan LTQ ion-trap mass spectrometer (San Jose, Calif.). The instrument modification involved by-passing the splitter to make a direct connection between the helium supply and the ion trap with the helium flow rate controlled using a metering flow valve (see FIG. 2). Ozone was introduced by attaching a plastic syringe containing ozone to a PEEKsil tubing restrictor (100 mm L×1/16" OD×0.025 mm ID) (SGE) connected to the helium supply line via a shut-off ball valve and T-junction downstream of the metering flow valve. Backing pressure was applied to the syringe using a syringe pump set to 25 μL/min. In the experiments, the helium flow rate was adjusted so that the ion gauge pressure read approximately $0.8\times10^{-5}$ Torr with the addition of oxygen and ozone (NB: this may not be an accurate pressure reading since the ion gauge is calibrated for helium). This was found to be the optimal pressure for mass accuracy, peak shape and ion abundance. An isolation width of 2-3 Th was used to isolate the ion of interest and a trapping time of 10 seconds was used to generate the spectra. For sodiated phosphatidylcholine-containing ions, two isolation steps were found to be useful in removing a collision induced fragment ion (59 Da neutral loss) from the spectra. This was done by using an isolation width of 2-3 Th (30 ms), followed by an isolation at 10 Th with a trapping time of 10 seconds. In most cases 50 scans were acquired to obtain a sufficient signal-to-noise ratio. To acquire MS spectra the flow rate of helium was decreased using the metering valve to obtain an ion gauge pressure of $0.5\times10^{-5}$ Torr. This achieved improved mass accuracy and peak shape.

Example 2

Determination of the Position of Unsaturation in a Phospholipid Having a Single Double Bond Electrospray ionization of a methanolic solution of the commercially available phosphatidylcholine standard, GPCho(16:0/9Z-18:1) (see structure below), produces an abundant ion at m/z 782 corresponding to the $[M+Na]^+$ adduct.

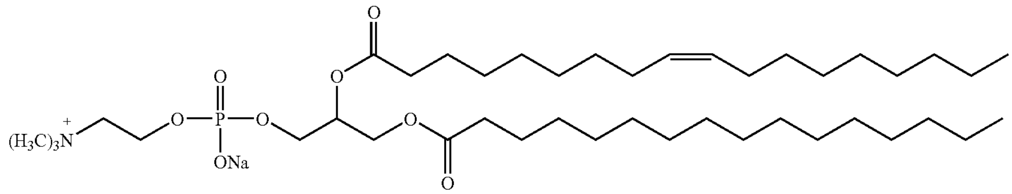

Figure 3:
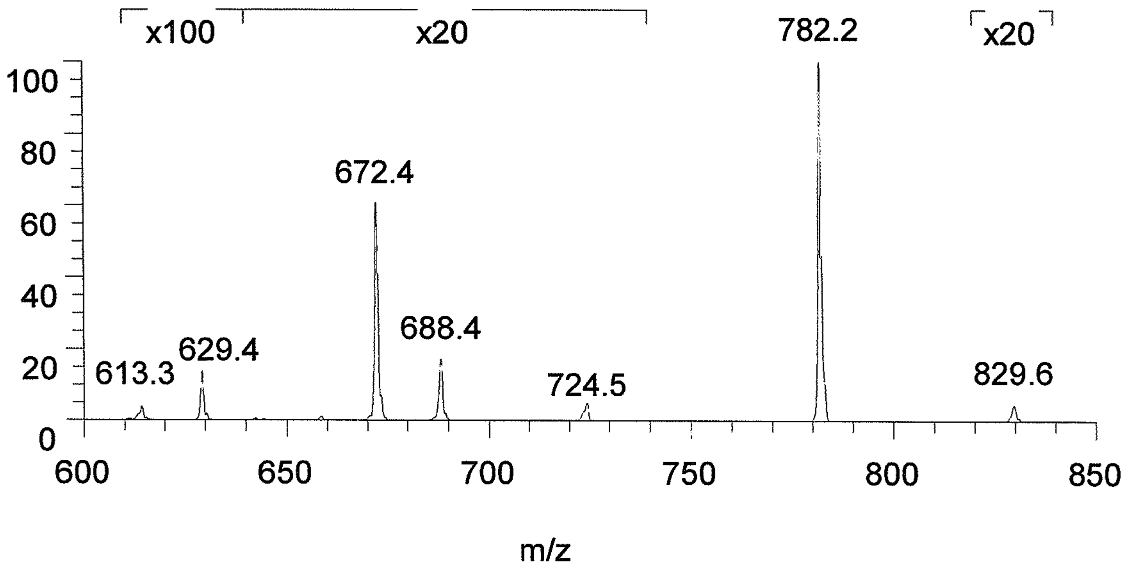
FIG. 3 shows the mass spectrum following reaction of ozone with the $[GPCho(16:0/9Z-18:1)+Na]^+$ adduct ion generated by electrospray ionization of a 1 μM solution of GPCho (16:0/9Z-18:1) in methanol with 200 μM sodium acetate. The pair of ions resulting from ozonolysis of the double bond are labelled with ■ and ● indicating aldehyde and Criegee ions, respectively.

Isolation and trapping of this ion within a quadrupole ion-trap mass spectrometer in the presence of ozone vapour for 10 seconds, yields the spectrum shown in FIG. 3. These data reveal that the gas phase ion-molecule reaction between the monounsaturated lipid and ozone yields two abundant product ions at m/z 672 and m/z 688 (see Scheme 1).

The formation of the m/z 672 ion represents a neutral loss of 110 Da and is therefore characteristic of a double bond in the 9 position. The m/z 672 ion is the sodium adduct of the aldehyde, 2-(9-oxononanoyl)-1-palmitoyl-sn-glycero-3-phosphocholine. The second chemically induced fragment ion at m/z 688 corresponds to a neutral loss of 94 Da from the precursor ion, thereby confirming that the double bond is located at position 9.

Less abundant ions at m/z 613 (not shown), 629 and 830 are also observed in FIG. 3. The latter ion corresponds to an addition of 48 Da to the $[GPCho(16:0/9Z-18:1)+Na]^+$ precursor ion and is most likely attributed to the secondary ozonide indicated in Scheme 1. The low abundance ions at m/z 613 and 629 correspond to neutral losses of 59 Da from the m/z 672 and 688 ions, respectively. The neutral loss of trimethylamine (59 Da) is a dominant fragmentation resulting from CID of sodium adducts ions of phosphatidylcholines. In this case it is likely that some of the energy liberated from the addition of ozone across the double bond (computed to be ca. 55 kcal $mol^{-1}$) is partitioned into the resulting fragment ions and drives subsequent decomposition via loss of trimethylamine.

Example 3

Determination of the Position of Unsaturation in Regioisomeric Phospholipids In this example, mass spectra (as sodium adducts) of two regioisomeric phospholipids GPCho(9Z-18:1/9Z-18:1) and GPCho(6Z-18:1/6Z-18:1) having the following structures were obtained.

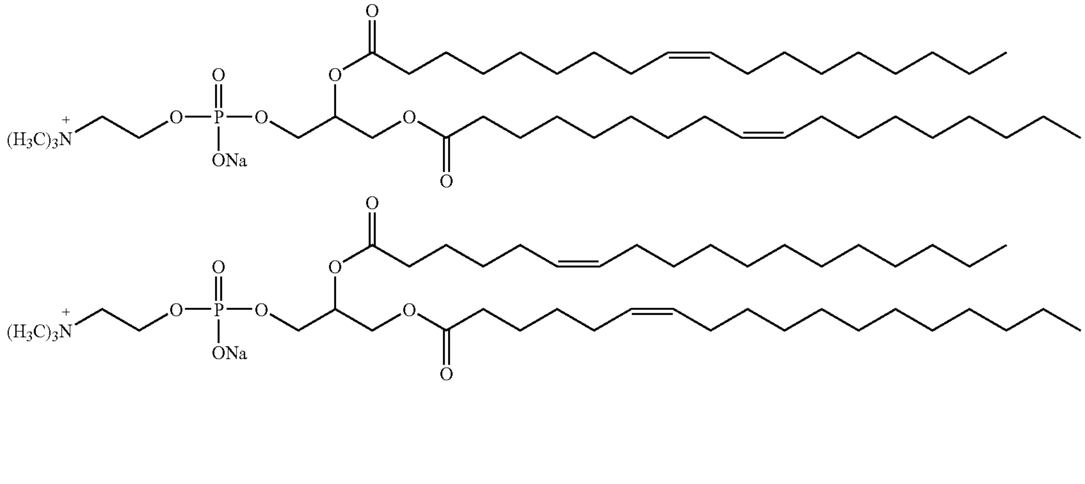

Figure 4A:
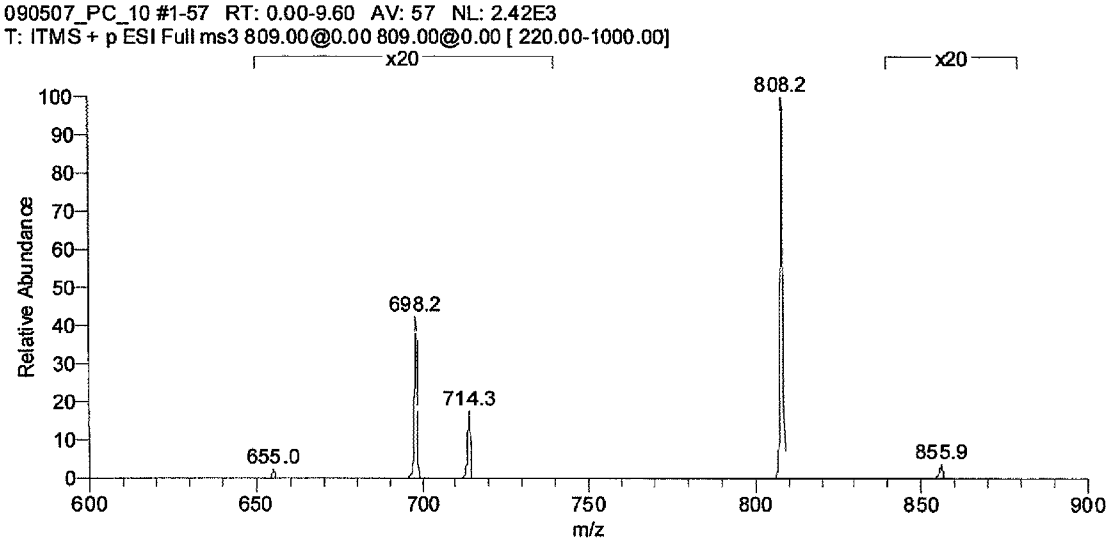
FIG. 4 shows mass spectra following reaction of the $[M+Na]^+$ ions of GPCho(9Z-18:1/9Z-18:1) (FIG. 4A) and GPCho(6Z-18:1/6Z-18:1) (FIG. 4B) with ozone. Both phospholipids were made to a concentration of 1 μM in methanol with 200 μM sodium acetate to aid sodium adduct formation during ESI.
Figure 4B:
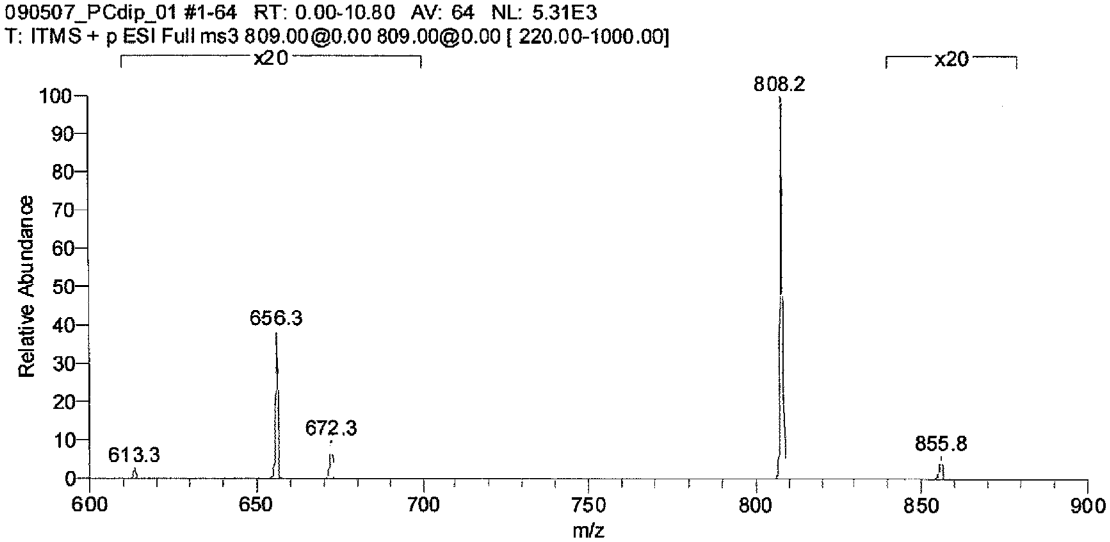

The ozone induced fragment ions are depicted in FIGS. 4A and 4B. Reference to FIGS. 4A and 4B shows that the ozone induced fragment ions are located at different m/z values for the two isomers.

In FIG. 4A ions are observed at m/z 714 and m/z 698, corresponding to losses of 94 and 110 Da respectively from the m/z 808 ion with which ozone was allowed to react. These losses are characteristic of double bonds at position 9 of a monounsaturated carbon chain.

In FIG. 4B ions are observed at m/z 672 and m/z 656, corresponding to losses of 136 and 152 Da respectively from the m/z 808 ion with which ozone was allowed to react. These losses are characteristic of a double bonds at position 12.

As is demonstrated by this Example, the ozone induced fragment ions clearly distinguish the two isomers, and allow assignment of the double bond position.

Example 4

Determination of the Position of Unsaturation of a Glycerophospholipid

The ozone induced dissociation of the $[M-H]^-$ ion of the acidic glycerophospholipid standard, GPGro(9Z-18:1/9Z-18:1) (shown below) was acquired using a 10 second reaction time (FIG. 5).

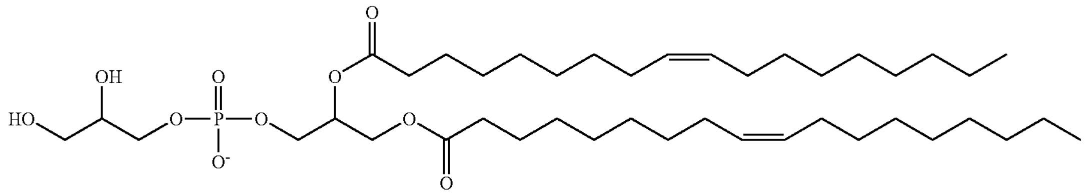

The mass spectrum of the [GPGro(9Z-18:1/9Z-18:1)—H] anion revealed a molecular ion at m/z 773, while the ozonolysis products were observed at m/z 663 and m/z 679. These fragment ions correspond to neutral losses of 110 and 94 Da respectively, indicating that the double bonds are located at position 9.

Example 5

Figure 6A:
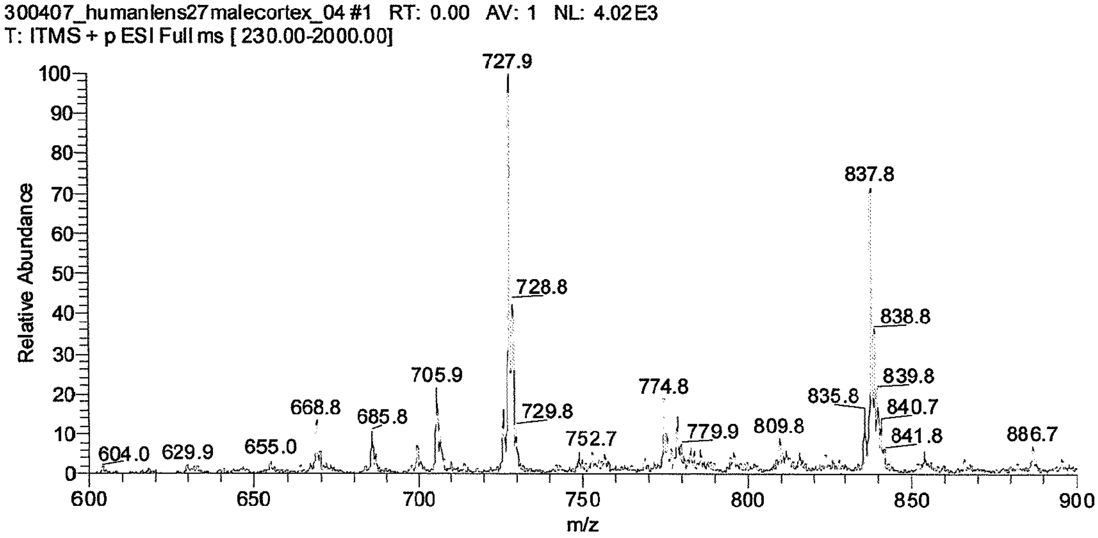
FIG. 6 shows mass spectra obtained from a lipid extract of a human lens. The positive ion ESI-MS spectrum reveals a sodium adduct at m/z 837 as the most abundant unsaturated phospholipid (FIG. 6A). The mass spectrum following reaction of the mass-selected m/z 837 ion $[SM(d18:0/24:1)+Na]^+$ with ozone is shown in FIG. 6B. Three sets of ozonolysis products were observed at different mass-to-charge ratios (labelled ■, ● and ▲) indicating the presence of three regioisomeric monounsaturated species at m/z 837 (where the double bonds are located at n=9, n=7 and n=5, respectively). The ion observed at m/z 684 results from a neutral loss of 59 Da (trimethylamine) from the abundant Criegee ion at m/z 743, while the ion at m/z 885 is assigned to the secondary ozonide resulting from the addition of $O_3$ (+48 Da).

Determination of the Position of Unsaturation in Regioisomeric Phospholipids in a Mixture Extracted from the Lens of a Human Eye The positive ion ESI-MS spectrum of a lipid extract from a human lens was recorded (see FIG. 6A) with most of the ions observed corresponding to sodium adducts of either phosphatidylcholines or sphingomyelins. In this spectrum, the two major ions observed are at m/z 727 and m/z 837. These ions can be assigned based on mass alone to sodium adducts of sphingomyelins.

Figure 6B:
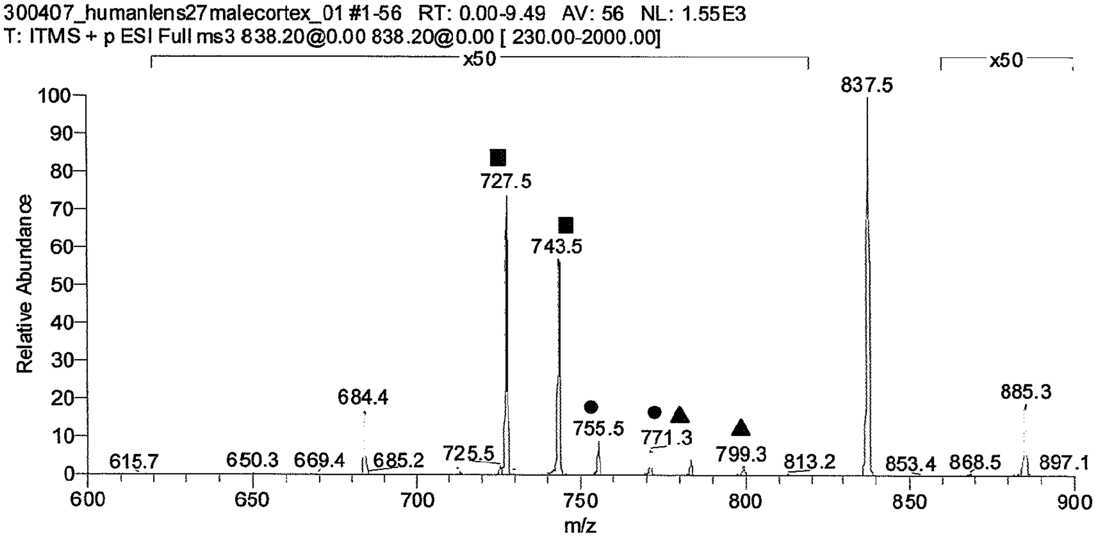

CID spectra of these ions identify them as dihydrosphingomyelins with 16:0 and 24:1 fatty acids bound to the sphinganine backbone (data not shown). Based on ESI-MS and CID analyses alone, the structure of the most abundant unsaturated phospholipid in the human lens would usually be assigned as the dihydroshingomyelin, SM(d18:0/15Z-24:1), where the amide linked fatty acid is assumed to be the n-9 nervonic acid (15Z-tetracosenoic acid), based on its previous observation in mammalian tissues. Such structure assignment ambiguities are removed by the spectrum following ozone induced dissociation of the mass-selected m/z 837 ion shown in FIG. 6B. This spectrum reveals three sets of ozonolysis products from this monounsaturated lipid indicating the presence of three distinct regioisomers.

The first product showed ions at m/z 799 and 783, indicating losses of 38 and 54 Da respectively. This was indicative of a double bond in the 5 position. This compound was assigned the following structure:

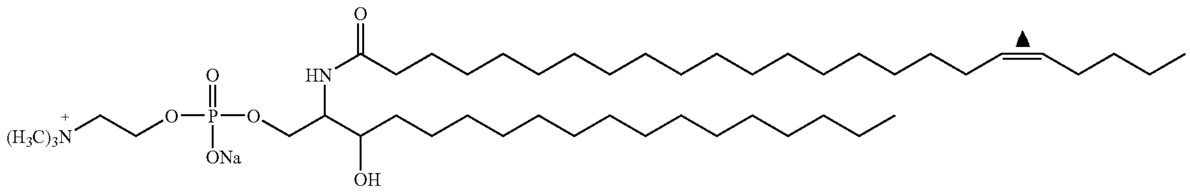

The second product showed ions at m/z 771 and 755, indicating losses of 66 and 82 Da respectively. This was indicative of a double bond in the 7 position. This compound was assigned the following structure:

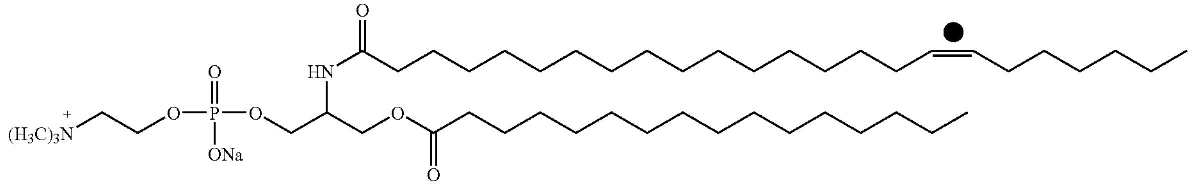

The third product showed ions at m/z 743 and 727, indicating losses of 94 and 110 respectively. This was indicative of a double bond in the 9 position. This compound was assigned the following structure:

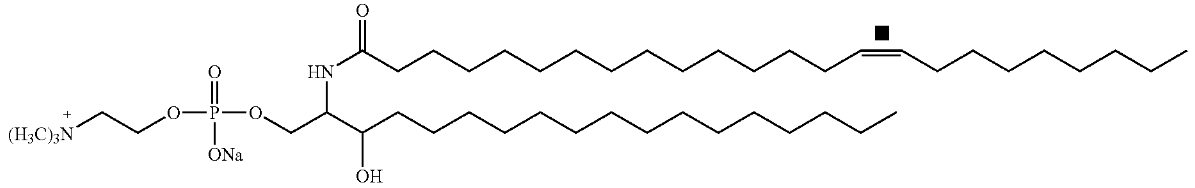

Example 6

Figure 7A:
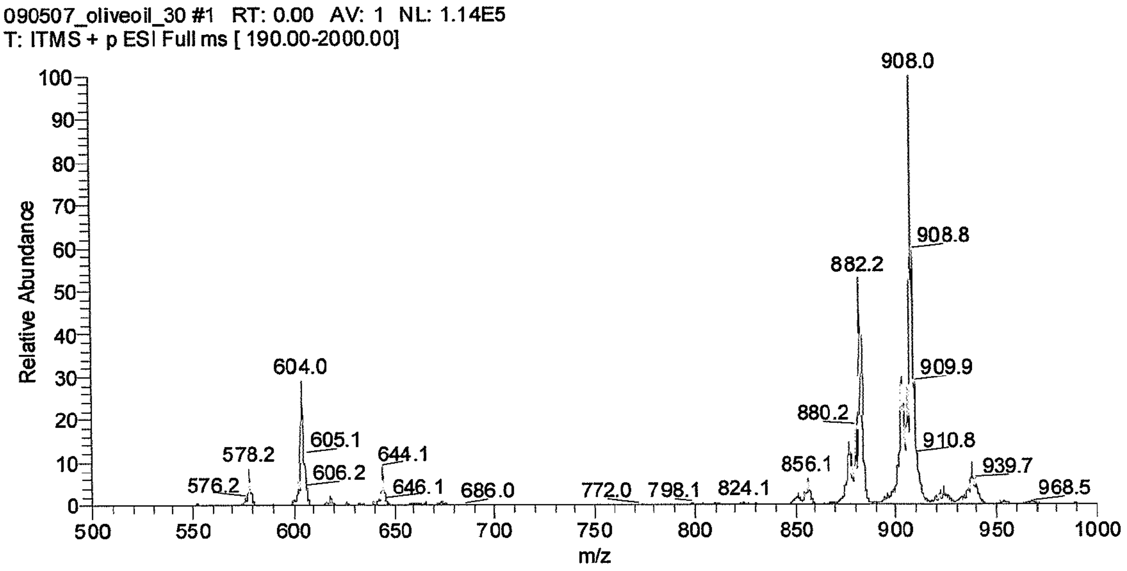
FIG. 7A shows the positive ion ESI-MS spectrum of a commercial sample of olive oil diluted to ca. 2 mg/mL in methanol with 100 μM sodium acetate. The ion at m/z 908 is the most abundant triacylglycerol.

Determination of the Position of Unsaturation in a Triacylglycerol in a Sample of Commercial Olive Oil The positive ion ESI-MS spectrum of a dilute methanolic solution of commercial olive oil in the presence of sodium acetate provides a base peak at m/z 908 (FIG. 7A) corresponding to the sodium adduct of the abundant triacylglyceride TG(18:1/18:1/18:1).

Figure 7B:
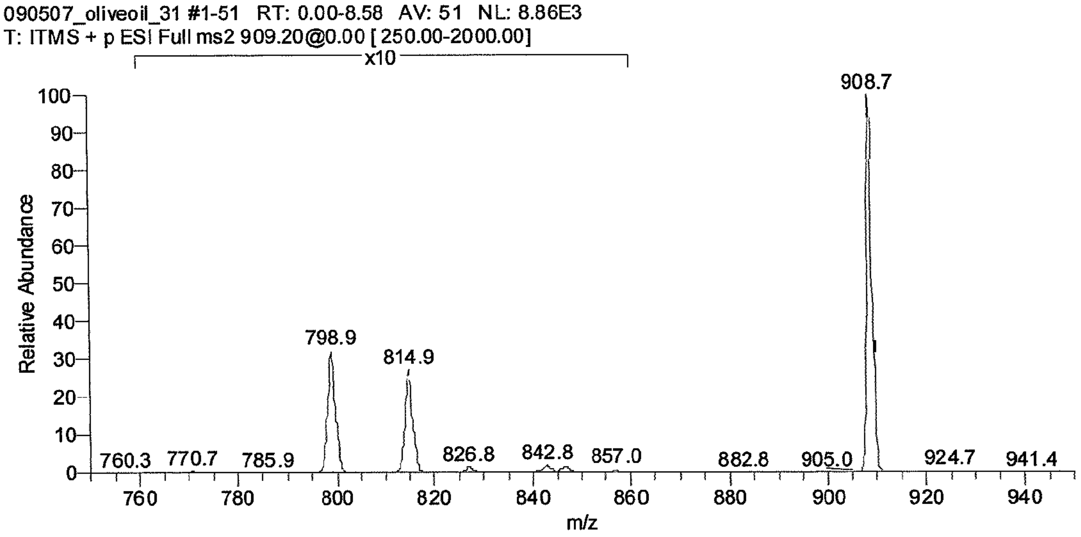
FIG. 7B shows the mass spectrum following reaction of the ion at m/z 908 with ozone. A single abundant set of ozone induced fragment ions is observed.

Mass-selection of this ion and exposure to ozone yields the spectrum presented in FIG. 7B showing two pronounced ozonolysis products at m/z 798 and 814 representing the neutral losses of 110 and 94 Da. These data identify the triacylglycerol as TG(9Z-18:1/9Z-18:1/9Z-18:1), which has the following structure, where only the stereochemistry is assumed:

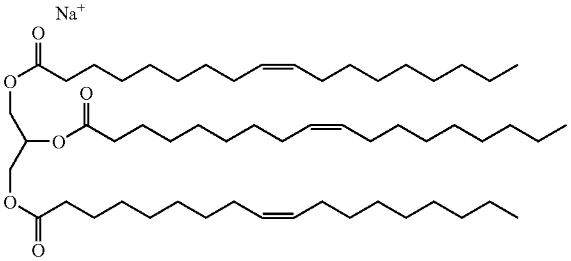

Example 7

Determination of the Position of Unsaturation in a Triacylglycerol Standard of Known Regiochemistry Triacylglycerols are an important and abundant class of lipid whose structural complexity makes them challenging targets for analysis. Recent developments have demonstrated that the combination of ESI-MS, CID and $MS^3$ experiments can be used to identify the fatty acid components of mass-selected triacylglycerols and even identify their relative positions on the glycerol backbone. As with phospholipids, the position of unsaturation within fatty acid substituents is generally assigned based only on the most naturally abundant fatty acids of the appropriate chain length and degree of unsaturation.

Figure 8:
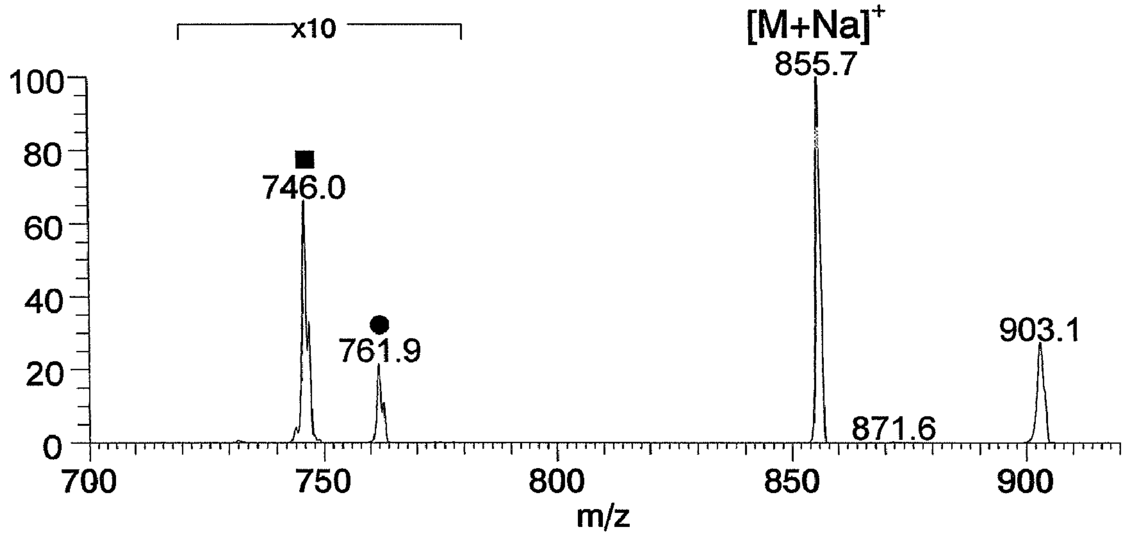
FIG. 8 shows the ozone induced dissociation (OzID) spectrum of the sodium adduct of the triacylglycerol standard, TG(16:0/9Z-18:1/16:0), generated from the electrospray of a 1 μM TG(16:0/9Z-18:1/16:0) methanolic solution with 100 μM sodium acetate. The ion at m/z 903 is assigned to the secondary ozonide resulting from the addition of $O_3$ (+48 Da). The pair of ions resulting from ozonolysis of the double bond are labelled with ■ and ● indicating aldehyde and Criegee ions, respectively.

FIG. 8 shows the spectrum following reaction of a sodium adduct (m/z 855) of the monounsaturated triacylglycerol standard, TG(16:0/9Z-18:1/16:0) with ozone for 10 seconds. Two structurally diagnostic fragments at m/z 746 and 761, corresponding to neutral losses of 110 and 94 Da respectively were obtained. These neutral losses are indicative of a double bond at position 9, and are consistent with the known structure of this triacylglycerol standard (see structure below). An abundant $[M+Na^+O_3]^+$ adduct ion is also observed in this spectrum at m/z 903 and is assigned as the secondary ozonide by analogy with Scheme 1.

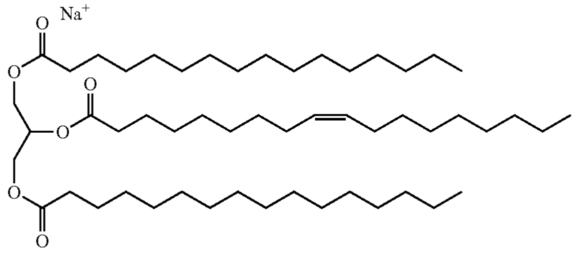

Example 8

Determination of the Position of Unsaturation in Polyunsaturated Phospholipids in a Cow Kidney Extract (1)

Figure 9A:
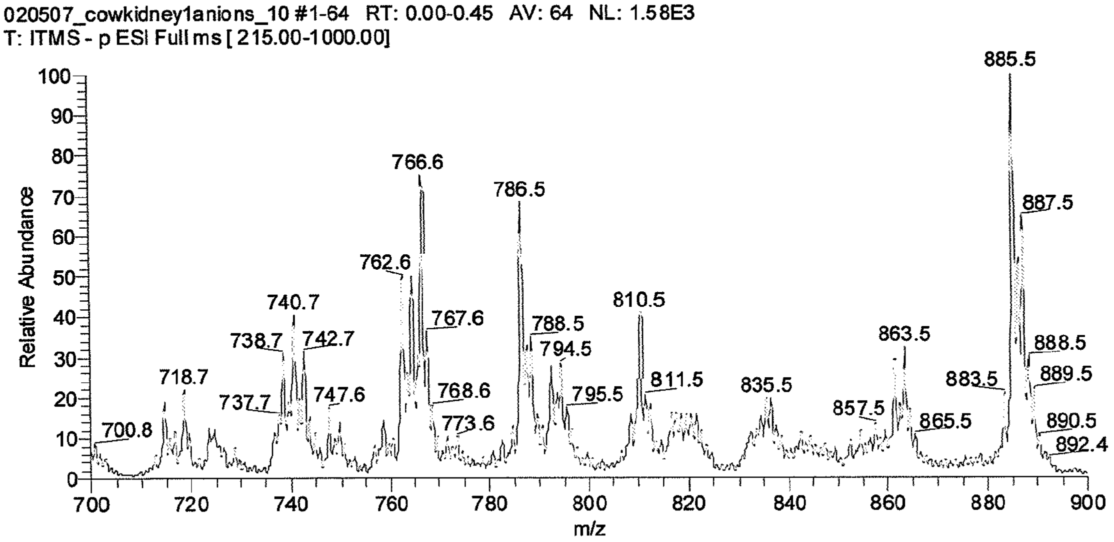
FIG. 9A shows a negative ion mass spectrum of a cow kidney extract. The m/z 887 ($[GPIns(18:0/20:3)—H]^-$) ion was selected for reaction with ozone.
Figure 9B:
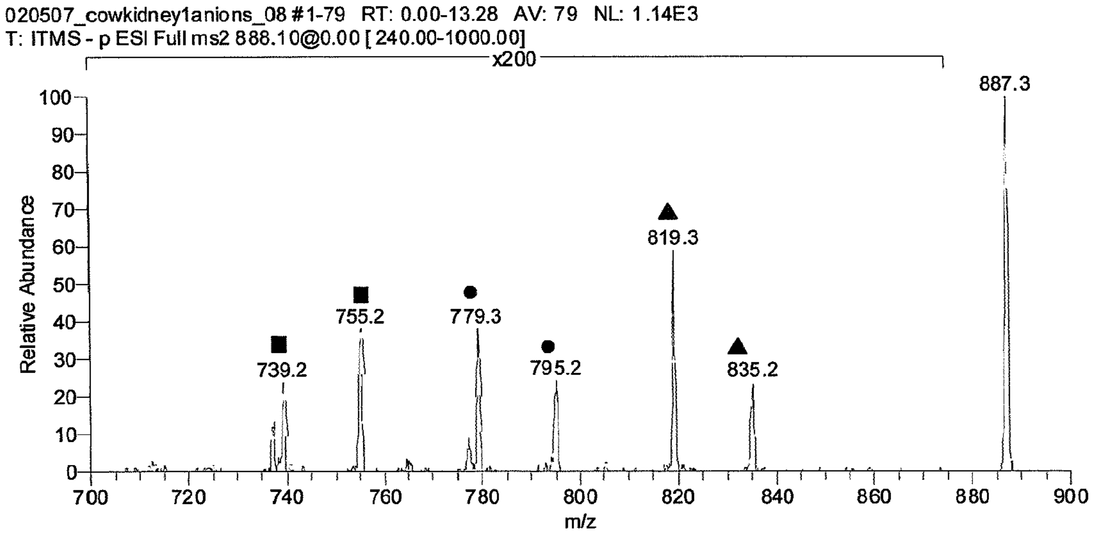
FIG. 9B shows the mass spectrum following reaction of the mass-selected ion at m/z 887 with ozone. Three sets of ozonolysis products from one polyunsaturated phospholipid are observed, indicating the presence of three distinct positions of unsaturation. Three pairs of ions resulting from ozonolysis of each double bond are labelled with ▲, ● and ■, indicating pairs of aldehyde and Criegee ions formed from ozonolysis of double bonds at the n=6, 9 and 12 positions, respectively.

A negative ion mass spectrum of a cow kidney extract was recorded (FIG. 9A). The m/z 887 ion was selected for reaction with ozone. Following reaction of the ion with ozone, three sets of ozonolysis products were obtained (FIG. 9B). With reference to Table 1, this compound was assigned the following structure:

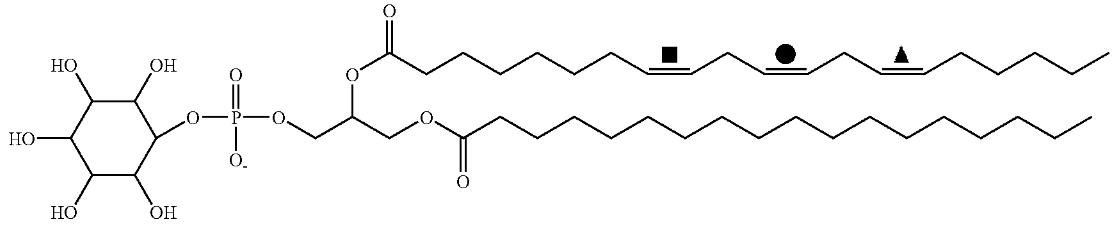

Example 9

Determination of the Position of Unsaturation in a Polyunsaturated Phospholipids in a Cow Kidney Extract (2)

Figure 10A:
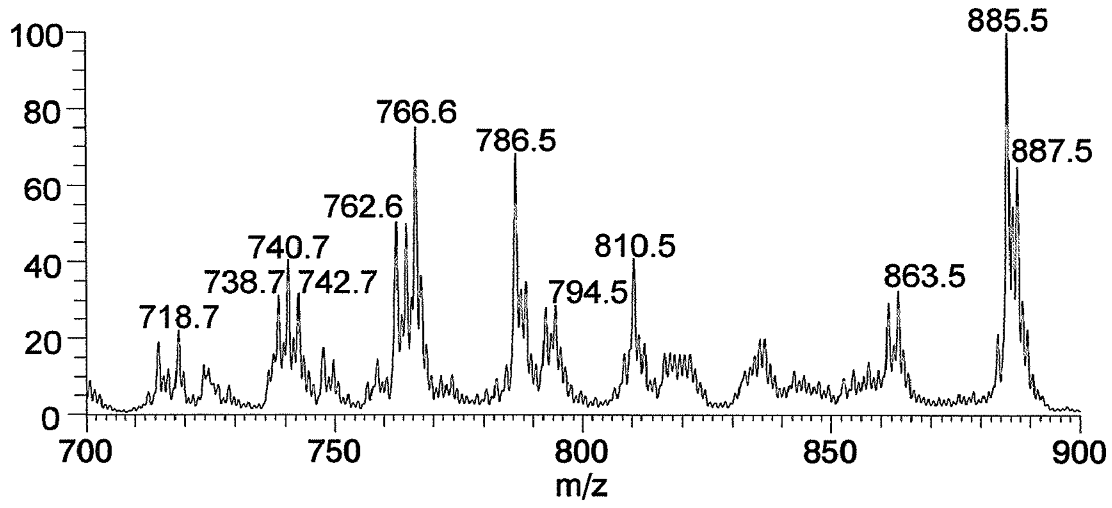
FIG. 10A shows the negative ion ESI-MS spectrum of a cow kidney lipid extract (ca. 40 μM in 2:1 methanol-chloroform).

The negative ion ESI-MS spectrum of a bovine kidney lipid extract is shown in FIG. 10A. This spectrum shows the $[M-H]^-$ of a suite of acidic phospholipids present within the extract. The two most abundant ions in this spectrum are observed at m/z 885 and 766 and, based on mass alone, can be tentatively assigned to the polyunsaturated phospholipids GPIns(38:4) and GPEtn(38:4) respectively. The structure of each ion was further elucidated by the respective negative ion CID spectra that confirm the headgroup assignments and identify the fatty acyl chains to be GPIns(18:0/20:4) and GPEtn(18:0/20:4) (data not shown).

Figure 10B:
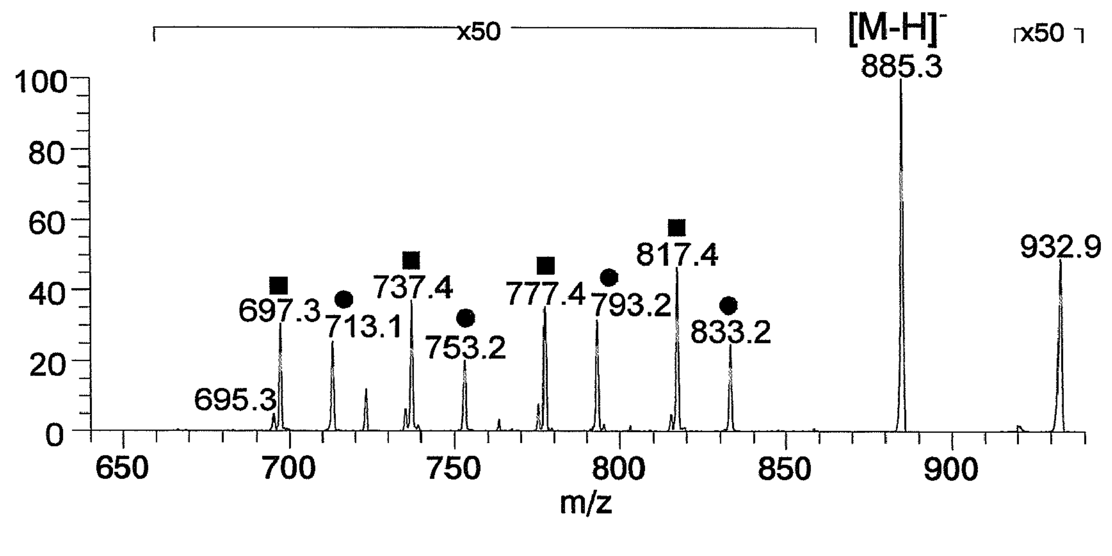
FIGS. 10B and 10C show the spectra obtained following reaction of the ions at m/z 885 ($[GPIns(18:0/20:4)—H]^-$) and 766 ($[GPEtn(18:0/20:4)—H]^-$) respectively, with ozone. The pairs of ions resulting from ozonolysis of each double bond are labelled with ■ and ● indicating aldehyde and Criegee ions, respectively.
Figure 10C:
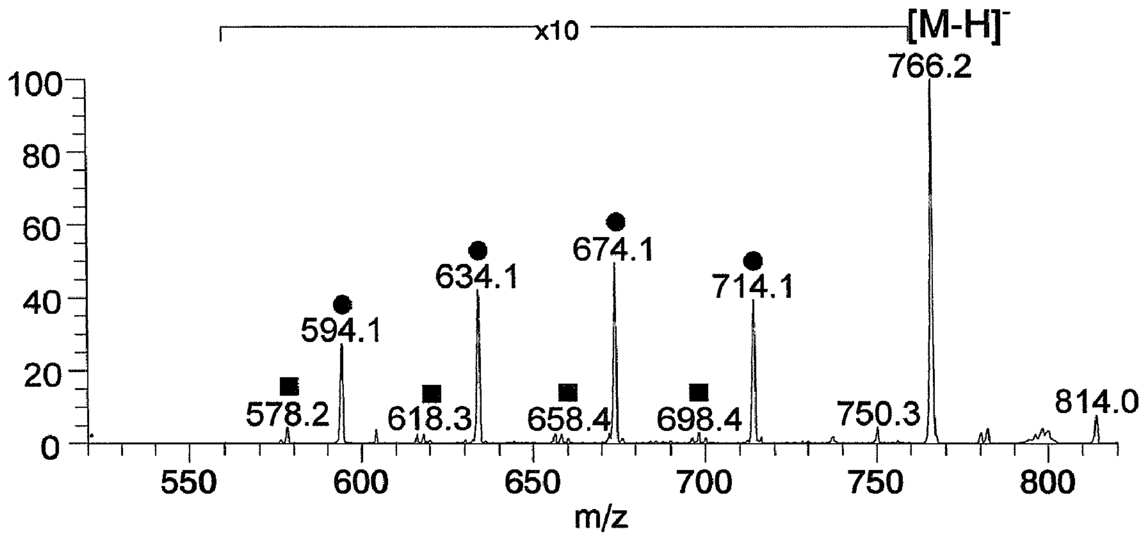

The position of unsaturation in each of the 20:4 radyls can be determined from the spectra shown in FIGS. 10B and 10C. Independent of the distinct headgroups of each phospholipid, both spectra display chemically induced fragment ions that correspond to neutral losses of 188, 172, 148, 132, 108, 92, 68 and 52 Da. For example, in FIG. 10B high mass fragment ions appear at m/z 833 and 817 and are separated by 16 Da, indicative of a Criegee and an aldehyde ion, respectively. The corresponding neutral losses of 52 and 68 Da suggest that these fragments result from ozonolysis of a double bond located at the 6 position. Subsequent pairs of fragment ions appear to lower mass by consecutive losses of 40 Da, indicative of the $C_3H_4$ units encountered in skip-conjugated polyunsaturated compounds and thus allowing the assignment of double bonds to positions 6, 9, 12 and 15. These positions of unsaturation unambiguously identify the 20:4 radyl as arachidonic acid as would usually be expected from the high natural abundance of this polyunsaturated fatty acid. Therefore, based on the combination of ESI-MS (FIG. 10A), CID (not shown) and ozone induced dissociation spectra (FIGS. 10B and 10C), these two bovine kidney derived phospholipids can be assigned as GPIns(18:0/5Z,8Z,11Z,14Z-20:4) and GPEtn (18:0/5Z,8Z,11Z,14Z-20:4), where only the stereochemistry is assumed. These phospholipids have the following structures.

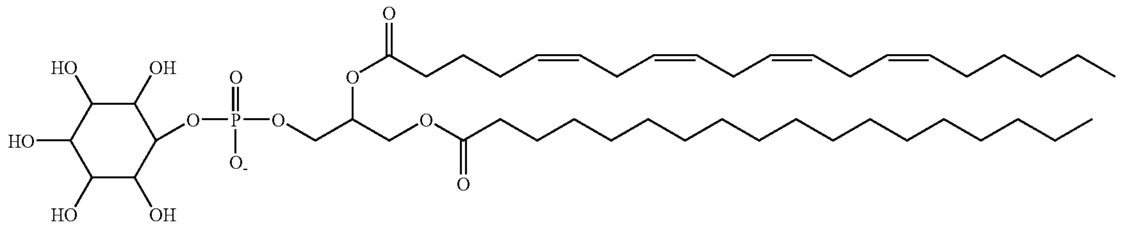

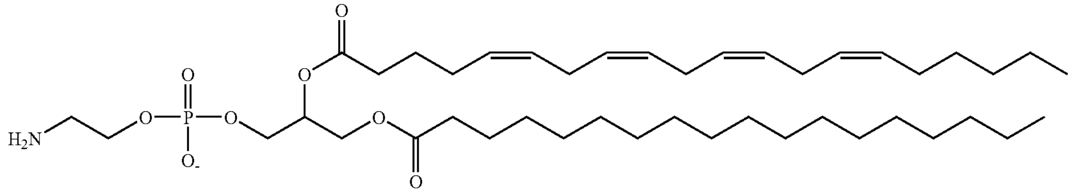

Example 10

Combination Structure Determination of Lipids in a Human Lens Extract

Figure 11A:
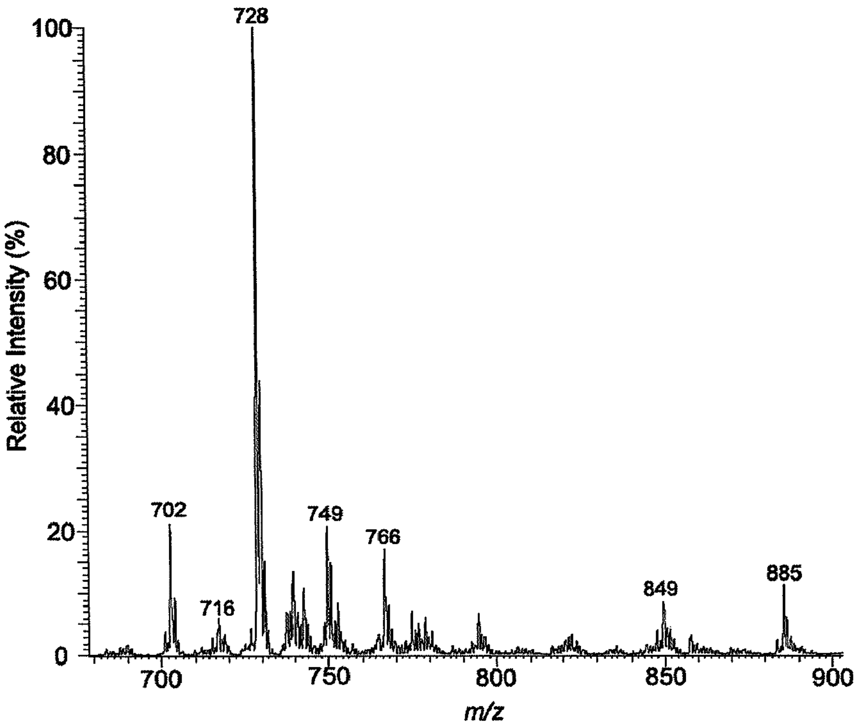
FIG. 11A shows the negative ion ESI-MS spectrum of a human lens lipid extract, all phospholipids within this spectrum appear as $[M-H]^-$ anions.
Figure 11B:
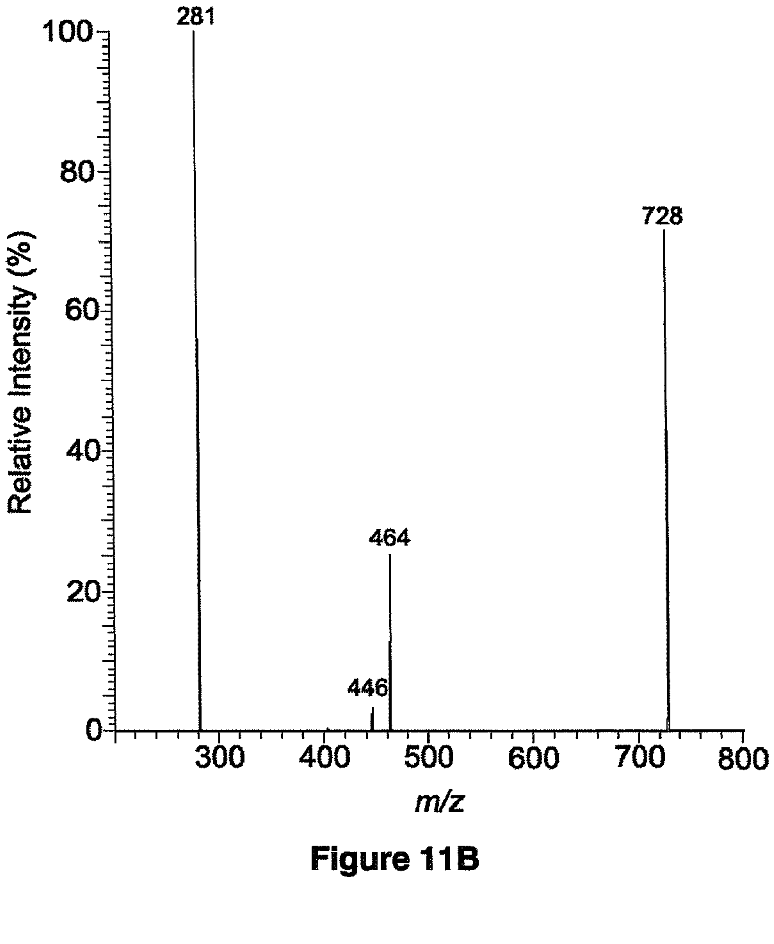
FIG. 11B shows the CID spectra of the m/z 728 anion mass-selected from the human lens.

The negative ion ESI-MS spectrum of a lipid extract from a human lens is shown in FIG. 11A revealing a suite of deprotonated phospholipid ions. While one must be careful in using relative ion abundances as a measure of lipid concentrations, the lipid at m/z 728 is clearly a significant lens phospholipid. Based on (i) the mass-to-charge ratio of the anion, (ii) the negative ion CID spectrum (FIG. 11B), and (iii) the observation of the corresponding cation in a m/z 141 positive ion precursor ion scan (data not shown), this lipid could be assigned to the phosphatidylethanolamines, GPEt (18:0p/18:1) or GPEt(18:1e/18:1), where the sn-1 fatty acid is attached via an alkenyl or an alkyl ether linkage, respectively.

Figure 11C:
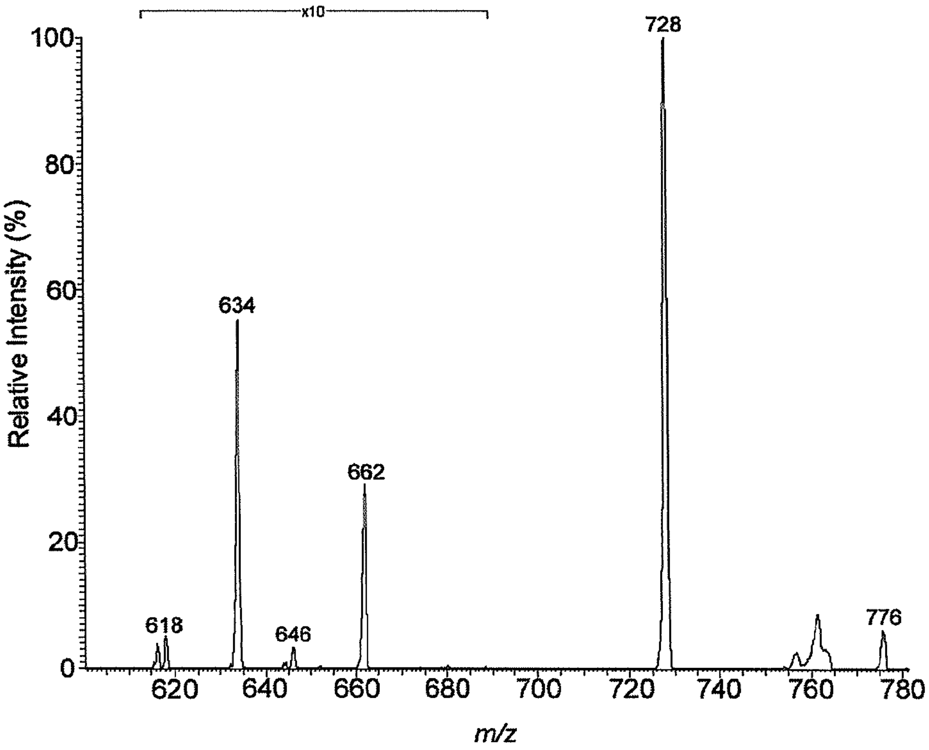
FIG. 11C shows the spectra obtained following reaction of the m/z 728 anion with ozone.
Figure 11D:
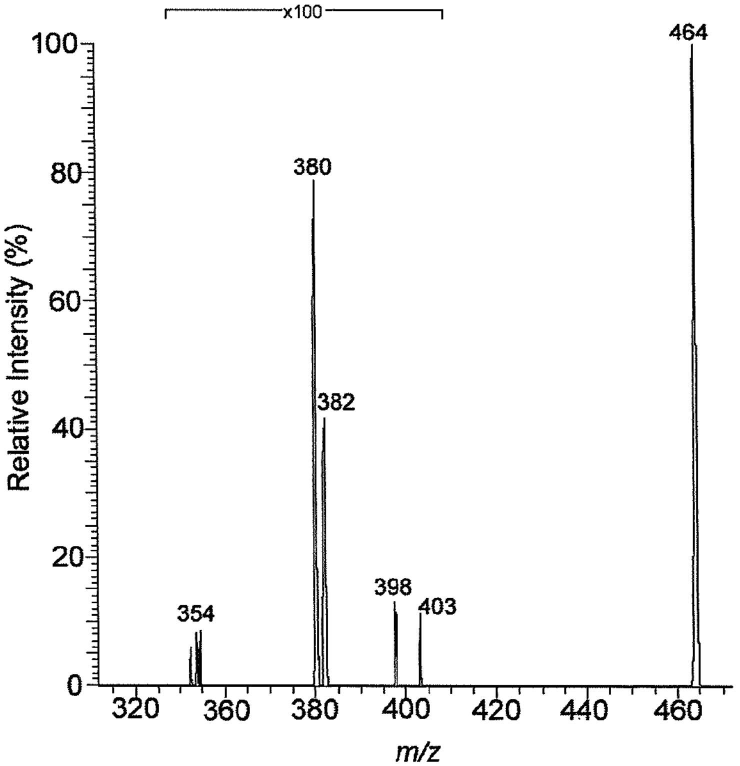
FIG. 11D shows the spectrum resulting from the ozonolysis of the mass selected m/z 464 resulting from the CID of the ion at m/z 728.

The spectrum obtained following ozone induced dissociation of the $[M-H]^-$ anion at m/z 728 (FIG. 11C), reveals ozone induced fragment ions at m/z 662, 646, 634 and 618. The high mass pair of ions correspond to neutral losses of 66 and 82 Da characteristic of an unsaturated carbon chain with a double bond in the 7 position, while the pair to lower mass correspond to neutral losses of 94 and 110 Da, which are ascribed to a double bond in the 9 position. Significantly, no ions were observed corresponding to the neutral losses of either 222 or 206 Da that might be expected from ozone induced cleavage of an 18-carbon alkenyl ether-linked fatty acid (i.e., 18:0p). The absence of both such ions is inconsistent with the putative plasmalogen structure, given the expected enhancement of ozone reactivity toward electron rich alkenyl ethers. These data are thus more suggestive of an unsaturated alkyl ether phospholipid, e.g., GPEt(18:1e/18:1), where one of the carbon chains has a 7 double bond, and the other a 9 double bond. To distinguish these two structural possibilities an $MS^3$ experiment was performed, wherein the m/z 464 CID ion—formed via loss of the esterified 18:1 fatty acid as a ketene from the m/z 728 precursor ion (FIG. 11C)—was itself mass-selected and allowed to react with ozone. This serial CID-ozone dissociation experiment (FIG. 11D) yielded abundant ions at m/z 398 and 382 via neutral losses of 66 and 82 Da, respectively. These ions can be assigned to ozonolysis of a 7 double bond on the ether linked 18:1 radyl and strongly suggests an overall assignment of GPEt(11Z-18:1e/9Z-18:1). The fragment ion at m/z 380 is consistent with water loss from the Criegee ion at m/z 398, the loss is similar to that observed for Criegee ions formed from the unsaturated phosphatidylglycerol (FIG. 5).

The claims defining the invention are as follows:

1. A method for determining the position of unsaturation in a compound comprising one or more unsaturated chains, the method comprising:

(i) ionizing the compound to provide ions;

(ii) selecting ions of a given mass-to-charge ratio;

(iii) allowing the selected ions to react with ozone to give ozone induced fragment ions;

(iv) mass analysis and detection of the ozone induced fragment ions formed in step (iii); and (v) determining the position of unsaturation in the compound based on the difference between the mass-to-charge ratio of the ions selected in step (ii), and the mass-to-charge ratio of one or more of the ozone induced fragment ions formed from the selected ions in step (iii).

2. The method of claim 1, wherein the unsaturation is one or more carbon-carbon-double bonds.

3. The method of claim 1, wherein the one or more unsaturated chains are alkenyl chains.

4. The method of claim 3, wherein the alkenyl chains terminate with a methyl or methylene group.

5. The method of claim 1, wherein the compound is selected from the group consisting of: polymers, lipids, metabolites, fatty acids, drugs, biological extracts and natural products.

6. The method of claim 1, wherein the one or more ozone induced fragment ions in step (v) is an ozone induced fragment ion comprising an aldehyde functional group, or an ozone induced fragment ion which is a Criegee ion.

7. The method of claim 1, which is used in conjunction with CID mass spectrometry.

8. The method of claim 3, further comprising the step of determining the stereochemistry of one or more carbon-carbon double bonds located in the one or more alkenyl chains based on the relative abundance of the ozone induced fragment ions.

9. A method for determining the position(s) of one or more carbon-carbon double bond(s) in a compound comprising one or more unsubstituted alkenyl chains, the method comprising:

(i) ionizing the compound to provide ions;

(ii) selecting ions of a given mass-to-charge ratio;

(iii) allowing the selected ions to react with ozone to give ozone induced fragment ions;

(iv) mass analysis and detection of the ozone induced fragment ions formed in step (iii); and (v) determining the position(s) of the double bond(s) in the compound according to any one of the following formulae (I) to (V):

$$n = \frac{m/z(M) - m/z(\text{Criegee}) + 32 + 2b}{14} \quad \text{(I)}$$

$$n = \frac{m/z(M) - m/z(\text{aldehyde}) + 16 + 2b}{14} \quad \text{(II)}$$

$$n = \frac{m/z(M) - m/z(\text{Criegee} - H_2O) + 14 + 2b}{14} \quad \text{(III)}$$

$$n = \frac{m/z(M) - m/z(\text{Criegee} - NMe_3) - 27 + 2b}{14} \quad \text{(IV)}$$

$$n = \frac{m/z(M) - m/z(\text{aldehyde} - NMe_3) - 43 + 2b}{14} \quad \text{(V)}$$

wherein:

"n" is an integer representing the position of the carbon-carbon double bond as numbered from the carbon of the terminal methyl or methylene group of the alkenyl chain;

"M" refers to the ions selected in step (ii);

"aldehyde" refers to the ozone induced fragment ion comprising an aldehyde functional group as a result of ozone induced dissociation of M;

"Criegee" refers to the ozone induced fragment ion located 16 mass units above the mass of the aldehyde fragment ion as a result of ozone induced dissociation of M;

"Criegee-$H_2O$" refers to the secondary fragment from the Criegee ion resulting from loss of water (−18 Da);

"Criegee-$NMe_3$" refers to the secondary fragment formed from the Criegee ion in phosphocholine-containing compounds resulting from loss of trimethylamine (−59 Da);

"aldehyde-$NMe_3$" refers to the secondary fragment formed from the aldehyde ion in phosphocholine-containing compounds resulting from loss of trimethylamine (−59 Da); and, "b" is an integer representing the number of double bonds between the position of fragmentation and the carbon of the terminal methyl or methylene group of the alkenyl chain.

10. A method for determining the position of a double bond in a compound of the general formula $M^1$-(CH═CH)-$M^2$, wherein $M^1$ and $M^2$ independently represent any organic residue, the method comprising:

(i) ionizing the compound to provide ions;

(ii) selecting ions of a given mass-to-charge ratio;

(iii) allowing the selected ions to react with ozone to give ozone induced fragment ions;

(iv) mass analysis and detection of the ozone induced fragment ions formed in step (iii);

and (v) determining the position of the double bond in the compound based on the relative masses of $M^1$ and $M^2$. Step (v) may be carried out as follows:

(a) determining the mass of $M^1$ by subtracting 29 Da from the observed mass of the ozone induced fragment ion comprising an aldehyde functional group; or (b) determining the mass of $M^1$ by subtracting 45 Da from the observed mass of the ozone induced fragment ion which is a Criegee ion;

(c) determining the mass of $M^2$ by solving the following formula for $M^2$: $M=M^1+M^2+C_2H_2$, wherein M is the mass of the ions selected in step (ii), and (d) assigning the position of the double bond based on the relative masses of $M^1$ and $M^2$.

11. A system for determining the position(s) of unsaturation in a compound comprising one or more unsaturated chains, the system comprising:

(i) means for ionizing the compound to provide ions;

(ii) means for selecting ions of a given mass-to-charge ratio;

(iii) means for allowing the selected ions to react with ozone to give ozone induced fragment ions;

(iv) means for mass analysing and detecting the ozone induced fragment ions formed in step (iii); and (v) means for determining the position of unsaturation in the compound based on the difference between the mass-to-charge ratio of the ions selected in step (ii), and the mass-to-charge ratio of one or more of the ozone induced fragment ions formed from the selected ions in step (iii).

* * * * *

UNITED STATES PATENT AND TRADEMARK OFFICE

CERTIFICATE OF CORRECTION

PATENT NO. : 7,771,943 B2
APPLICATION NO. : 11/843199
DATED : August 10, 2010
INVENTOR(S) : Stephen Blanksby et al.

It is certified that error appears in the above-identified patent and that said Letters Patent is hereby corrected as shown below:

IN THE CLAIMS:

In column 32, line 60, claim 10:

Delete “$M^2$.”

Insert -- $M^2$, --

In column 32, line 61, claim 10:

Delete “Step (v) may be”

Insert -- Wherein step (v) is --

Signed and Sealed this
Thirteenth Day of March, 2012

David J. Kappos
*Director of the United States Patent and Trademark Office*